(12) United States Patent
Roy et al.

(10) Patent No.: US 11,191,899 B2
(45) Date of Patent: Dec. 7, 2021

(54) INFUSION SYSTEMS AND RELATED PERSONALIZED BOLUSING METHODS

(71) Applicant: MEDTRONIC MINIMED, INC., Northridge, CA (US)

(72) Inventors: Anirban Roy, Agoura Hills, CA (US); Benyamin Grosman, Valley Village, CA (US); Neha J. Parikh, West Hills, CA (US); Di Wu, Glendale, CA (US); Louis J. Lintereur, Stevenson Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 184 days.

(21) Appl. No.: 16/547,512

(22) Filed: Aug. 21, 2019

(65) Prior Publication Data

US 2020/0254175 A1    Aug. 13, 2020

Related U.S. Application Data

(60) Provisional application No. 62/856,665, filed on Jun. 3, 2019, provisional application No. 62/804,680, filed on Feb. 12, 2019, provisional application No. 62/804,677, filed on Feb. 12, 2019.

(51) Int. Cl.
*A61M 5/172* (2006.01)
*A61M 5/142* (2006.01)
*G16H 20/17* (2018.01)

(52) U.S. Cl.
CPC ...... *A61M 5/1723* (2013.01); *A61M 5/14244* (2013.01); *G16H 20/17* (2018.01); *A61M 2005/14208* (2013.01); *A61M 2005/14272* (2013.01); *A61M 2005/1726* (2013.01); *A61M 2205/52* (2013.01); *A61M 2230/201* (2013.01)

(58) Field of Classification Search
CPC .... G16H 20/17; G16H 50/20; A61B 5/14532; A61B 5/002; A61B 5/4866; A61B 5/7275; A61M 5/1723; A61M 5/14276
See application file for complete search history.

(56) References Cited

U.S. PATENT DOCUMENTS

| | | |
|---|---|---|
| 4,562,751 A | 1/1986 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |

(Continued)

*Primary Examiner* — Manuel A Mendez

(57) ABSTRACT

Infusion systems, infusion devices, and related operating methods are provided. A method of operating an infusion device involves obtaining an input qualitative event attribute, such as a meal size, obtaining a quantitative event attribute associated with the qualitative event attribute that is representative of a subset of historical events for a patient associated with the qualitative event attribute, such as a representative carbohydrate amount for the qualitative meal size, and thereafter determine a dosage of fluid based at least in part on the quantitative event attribute and operate the infusion device to deliver the dosage of the fluid to the patient.

19 Claims, 10 Drawing Sheets

(56) References Cited

U.S. PATENT DOCUMENTS

| | | |
|---|---|---|
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2013/0338630 A1 | 12/2013 | Agrawal et al. |
| 2014/0066889 A1 | 3/2014 | Grosman et al. |
| 2018/0161495 A1 | 6/2018 | Estes |
| 2018/0169334 A1 | 6/2018 | Grosman et al. |
| 2018/0197628 A1* | 7/2018 | Wei ................... A61B 5/14532 |
| 2019/0175833 A1* | 6/2019 | Sjolund ............... A61B 5/0022 |

* cited by examiner

INFUSION SYSTEMS AND RELATED PERSONALIZED BOLUSING METHODS

CROSS-REFERENCE TO RELATED APPLICATION(S)

This application claims the benefit of U.S. Provisional Patent Application Ser. No. 62/856,665, filed Jun. 3, 2019, U.S. Provisional Patent Application Ser. No. 62/804,677, filed Feb. 12, 2019, and U.S. Provisional Patent Application Ser. No. 62/804,680, filed Feb. 12, 2019, the contents of which are incorporated by reference herein in their entirety.

TECHNICAL FIELD

Embodiments of the subject matter described herein relate generally to medical devices, and more particularly, embodiments of the subject matter relate to automatically adapting operations of a fluid infusion device in a personalized manner.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the user's activities or other condition(s) experienced by the user.

Managing a diabetic's blood glucose level is also complicated by the user's consumption of meals or carbohydrates. Often, a user manually administers a bolus of insulin at or around meal time to mitigate postprandial hyperglycemia. To effectively mitigate postprandial hyperglycemia while also avoiding postprandial hypoglycemia, the user is often required to estimate the amount of carbohydrates being consumed, with that amount of carbohydrates then being utilized to determine the appropriate bolus dosage. While undesirably increasing the burden on the patient for managing his or her therapy, manual errors such as miscounting carbohydrates or failing to initiate a bolus in a timely manner can also reduce the therapy effectiveness. Accordingly, there is a need facilitate improved glucose control that reduces the likelihood of manual errors while also reducing patient workload.

BRIEF SUMMARY

Infusion devices, infusion systems, and related operating methods are provided. An embodiment of a method of operating an infusion device capable of delivering insulin to a patient involves a control system associated with the infusion device receiving an input qualitative meal size via a user interface, identifying a patient-specific carbohydrate amount representative of a clustered subset of historical meal events for the patient that are assigned to or otherwise associated with the input qualitative meal size, determining a bolus dosage of the insulin for the input qualitative meal size based at least in part on the patient-specific carbohydrate amount, and operating the infusion device (or an actuation arrangement thereof) to deliver the bolus dosage of the insulin to the patient.

Another embodiment of a method of operating an infusion device capable of delivering fluid to a patient is provided. The method involves a control system associated with the infusion device obtaining a qualitative event attribute via a user interface, obtaining a quantitative event attribute associated with the qualitative event attribute, wherein the quantitative event attribute is representative of a subset of historical events for the patient associated with the qualitative event attribute, and determining a dosage of the fluid based at least in part on the quantitative event attribute, with the infusion device being subsequently operated to deliver the determined dosage of the fluid to the patient.

An embodiment of an infusion system is also provided. The infusion system includes an actuation arrangement operable to deliver insulin to a patient, a user interface to receive an input qualitative meal size, a data storage element to maintain historical meal data associated with historical meal events for the patient, and a control system coupled to the actuation arrangement, the user interface, and the data storage element to identify a patient-specific carbohydrate amount representative of a clustered subset of the historical meal events associated with the input qualitative meal size, determine a meal bolus dosage of the insulin for the input qualitative meal size based at least in part on the patient-specific carbohydrate amount and operate the actuation arrangement to deliver the meal bolus dosage of the insulin to the patient.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
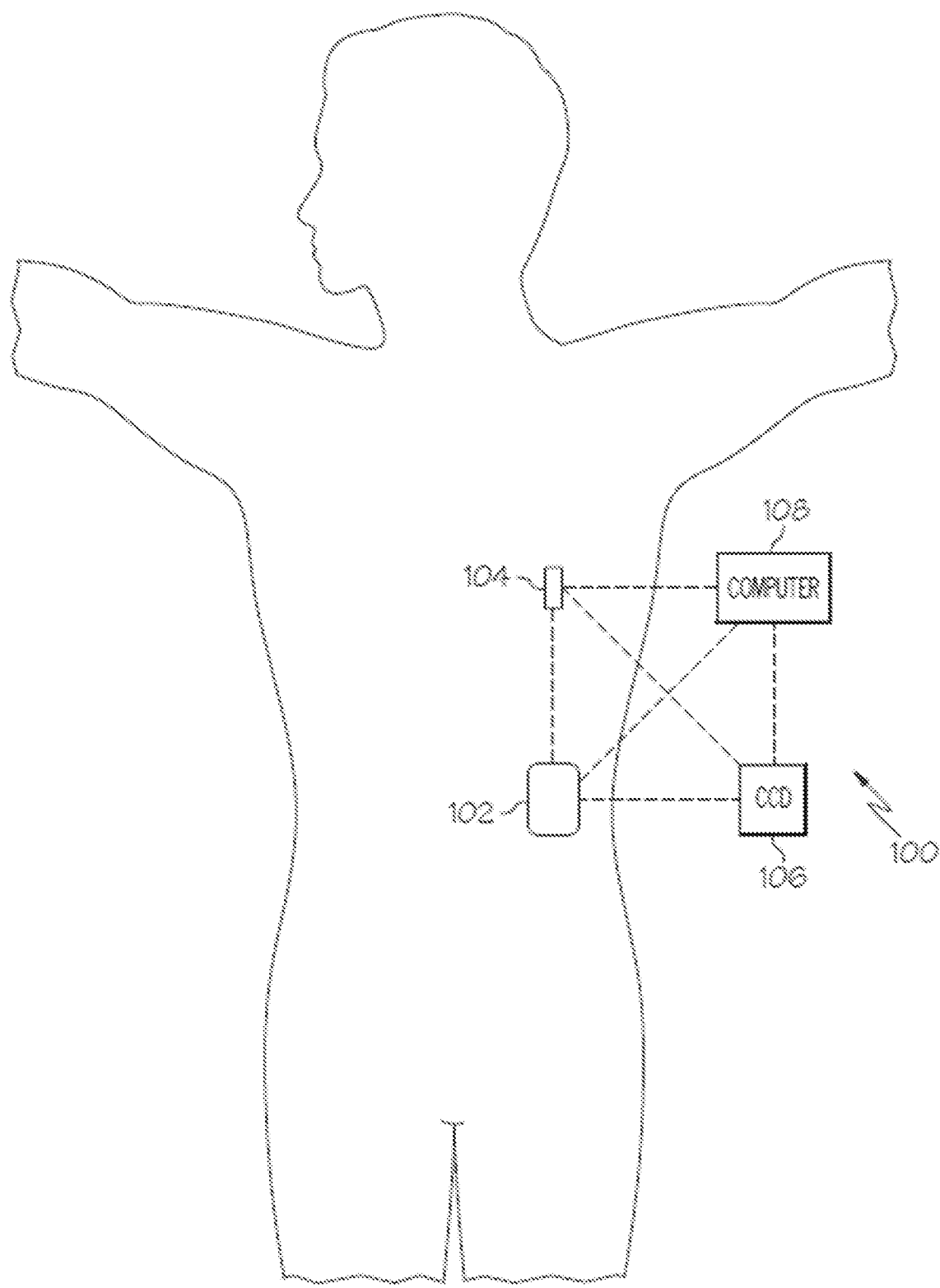
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to displace a plunger (or stopper) or other delivery mechanism to deliver a dosage of fluid, such as insulin, from a reservoir provided within the fluid infusion device to the body of a patient. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below in the context of FIGS. 5-9, in one or more exemplary embodiments, meal bolus dosages are calculated or otherwise determined in a personalized, patient-specific manner. Rather than counting carbohydrates or otherwise quantifying a meal size, the user can input a qualitative meal size, such as small, medium, large, and the like. Based on the patient's historical meal data and historical glucose measurement data, historical meal events are clustered into different subsets or groups which are associated with or otherwise assigned to different qualitative meal sizes for the particular patient. A patient-specific carbohydrate amount representative of the clustered subset of historical meal events associated with an input qualitative meal size is utilized to calculate or otherwise determine a meal bolus dosage amount of insulin to be delivered in response to the input qualitative meal size in a personalized manner without any carbohydrate counting. While the subject matter is described herein primarily in the context of a meal bolus dosage of insulin being delivered in connection with a meal event, the subject matter described herein is not limited to meals, and may be implemented in an equivalent manner in the context of a correction bolus that may be manually-initiated in association with exercise or any other activity, condition, or event that is likely to influence the patient's response (or sensitivity) to the fluid being administered (e.g., by clustering historical events according to qualitative event attributes to determine one or more quantitative event attribute(s) representative of a qualitative event attribute).

Infusion System Overview

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589, 229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
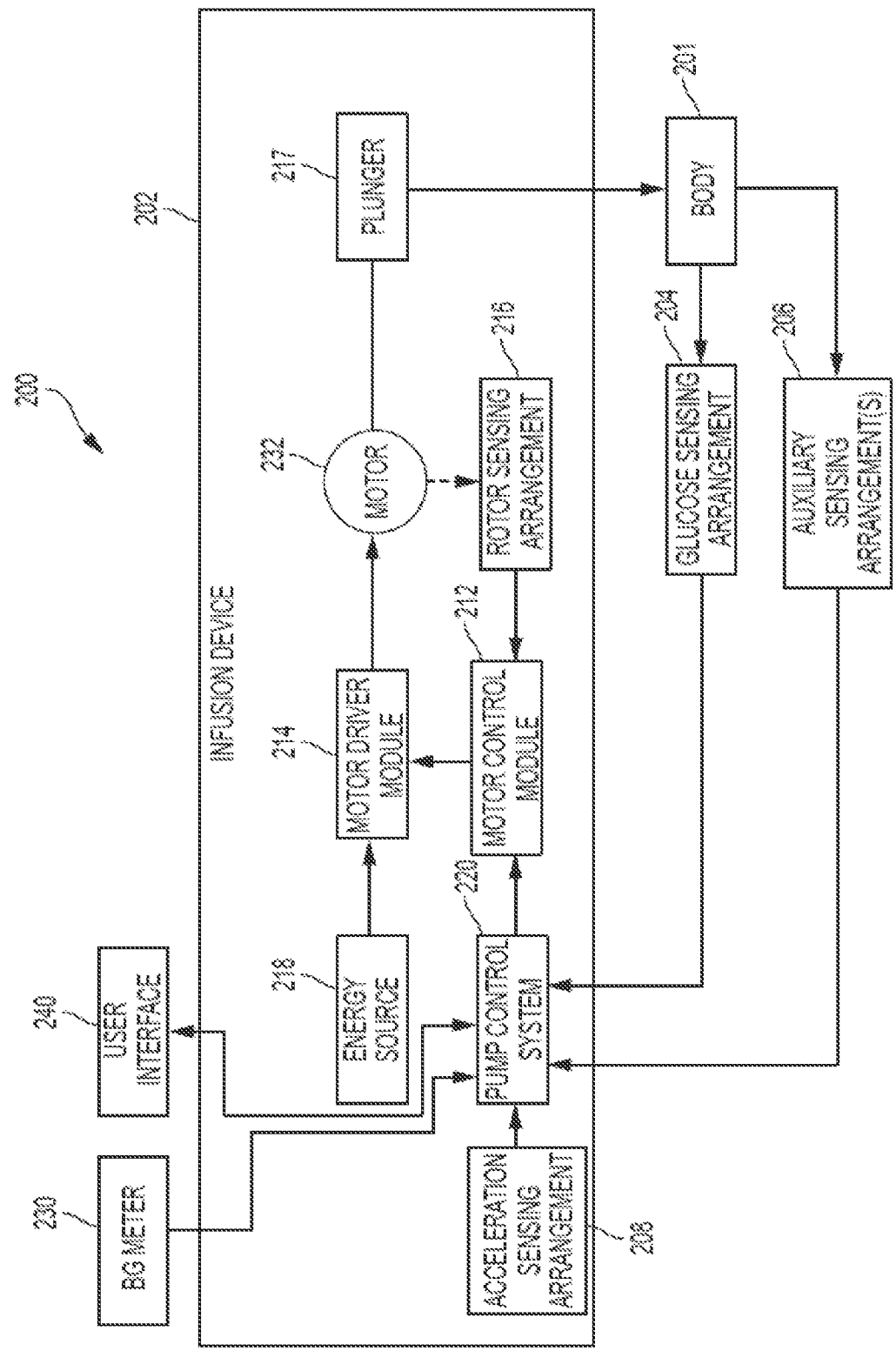
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In exemplary embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 204 may alternatively be referred to herein as the sensor glucose value, the sensed glucose value, or variants thereof.

In the illustrated embodiment, the control system 200 also includes one or more additional sensing arrangements 206, 208 configured to sense, detect, measure or otherwise quantify a characteristic of the body 201 of the patient that is indicative of a condition in the body 201 of the patient. In this regard, in addition to the glucose sensing arrangement 204, one or more auxiliary sensing arrangements 206 may be worn, carried, or otherwise associated with the body 201 of the patient to measure characteristics or conditions of the patient (or the patient's activity) that may influence the patient's glucose levels or insulin sensitivity. For example, a heart rate sensing arrangement 206 could be worn on or otherwise associated with the patient's body 201 to sense, detect, measure or otherwise quantify the patient's heart rate, which, in turn, may be indicative of exercise (and the intensity thereof) that is likely to influence the patient's glucose levels or insulin response in the body 201. In yet another embodiment, another invasive, interstitial, or subcutaneous sensing arrangement 206 may be inserted into the body 201 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 206 could be realized as a standalone component worn by the patient, or alternatively, the auxiliary sensing arrangement(s) 206 may be integrated with the infusion device 202 or the glucose sensing arrangement 204.

The illustrated control system 200 also includes an acceleration sensing arrangement 208 (or accelerometer) that may be worn on or otherwise associated with the patient's body 201 to sense, detect, measure or otherwise quantify an acceleration of the patient's body 201, which, in turn, may be indicative of exercise or some other condition in the body 201 that is likely to influence the patient's insulin response. While the acceleration sensing arrangement 208 is depicted as being integrated into the infusion device 202 in FIG. 2, in alternative embodiments, the acceleration sensing arrangement 208 may be integrated with another sensing arrangement 204, 206 on the body 201 of the patient, or the acceleration sensing arrangement 208 may be realized as a separate standalone component that is worn by the patient.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an actuation arrangement, such as a motor 232, to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. As described in greater detail, in one or more exemplary embodiments, the pump control system 220 automatically adjusts or adapts one or more parameters or other control information used to generate commands for operating the motor 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 associated with the infusion device 202 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes a motor control module 212 coupled to a motor 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). A motor driver module 214 is coupled between an energy source 218 and the motor 232. The motor control module 212 is coupled to the motor driver module 214, and the motor control module 212 generates or otherwise provides command signals that operate the motor driver module 214 to provide current (or power) from the energy source 218 to the motor 232 to displace the plunger 217 in response to receiving, from a pump control system 220, a dosage command indicative of the desired amount of fluid to be delivered.

In exemplary embodiments, the energy source 218 is realized as a battery housed within the infusion device 202 that provides direct current (DC) power. In this regard, the motor driver module 214 generally represents the combination of circuitry, hardware and/or other electrical components configured to convert or otherwise transfer DC power provided by the energy source 218 into alternating electrical signals applied to respective phases of the stator windings of the motor 232 that result in current flowing through the stator windings that generates a stator magnetic field and causes the rotor of the motor 232 to rotate. The motor control module 212 is configured to receive or otherwise obtain a commanded dosage from the pump control system 220, convert the commanded dosage to a commanded translational displacement of the plunger 217, and command, signal, or otherwise operate the motor driver module 214 to cause the rotor of the motor 232 to rotate by an amount that produces the commanded translational displacement of the plunger 217. For example, the motor control module 212 may determine an amount of rotation of the rotor required to produce translational displacement of the plunger 217 that achieves the commanded dosage received from the pump control system 220. Based on the current rotational position (or orientation) of the rotor with respect to the stator that is indicated by the output of the rotor sensing arrangement 216, the motor control module 212 determines the appropriate sequence of alternating electrical signals to be applied to the respective phases of the stator windings that should rotate the rotor by the determined amount of rotation from its current position (or orientation). In embodiments where the motor 232 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 212 operates the motor driver module 214 to apply the determined alternating electrical signals (e.g., the command signals) to the stator windings of the motor 232 to achieve the desired delivery of fluid to the patient.

When the motor control module 212 is operating the motor driver module 214, current flows from the energy source 218 through the stator windings of the motor 232 to produce a stator magnetic field that interacts with the rotor magnetic field. In some embodiments, after the motor control module 212 operates the motor driver module 214 and/or motor 232 to achieve the commanded dosage, the motor control module 212 ceases operating the motor driver module 214 and/or motor 232 until a subsequent dosage command is received. In this regard, the motor driver module 214 and the motor 232 enter an idle state during which the motor driver module 214 effectively disconnects or isolates the stator windings of the motor 232 from the energy source 218. In other words, current does not flow from the energy source 218 through the stator windings of the motor 232 when the motor 232 is idle, and thus, the motor 232 does not consume power from the energy source 218 in the idle state, thereby improving efficiency.

Depending on the embodiment, the motor control module 212 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 212. The computer-executable programming instructions, when read and executed by the motor control module 212, cause the motor control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may implemented by or otherwise integrated into the pump control system 220, or vice versa. Similarly, in practice, the features and/or functionality of the motor control module 212 may implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Figure 3:
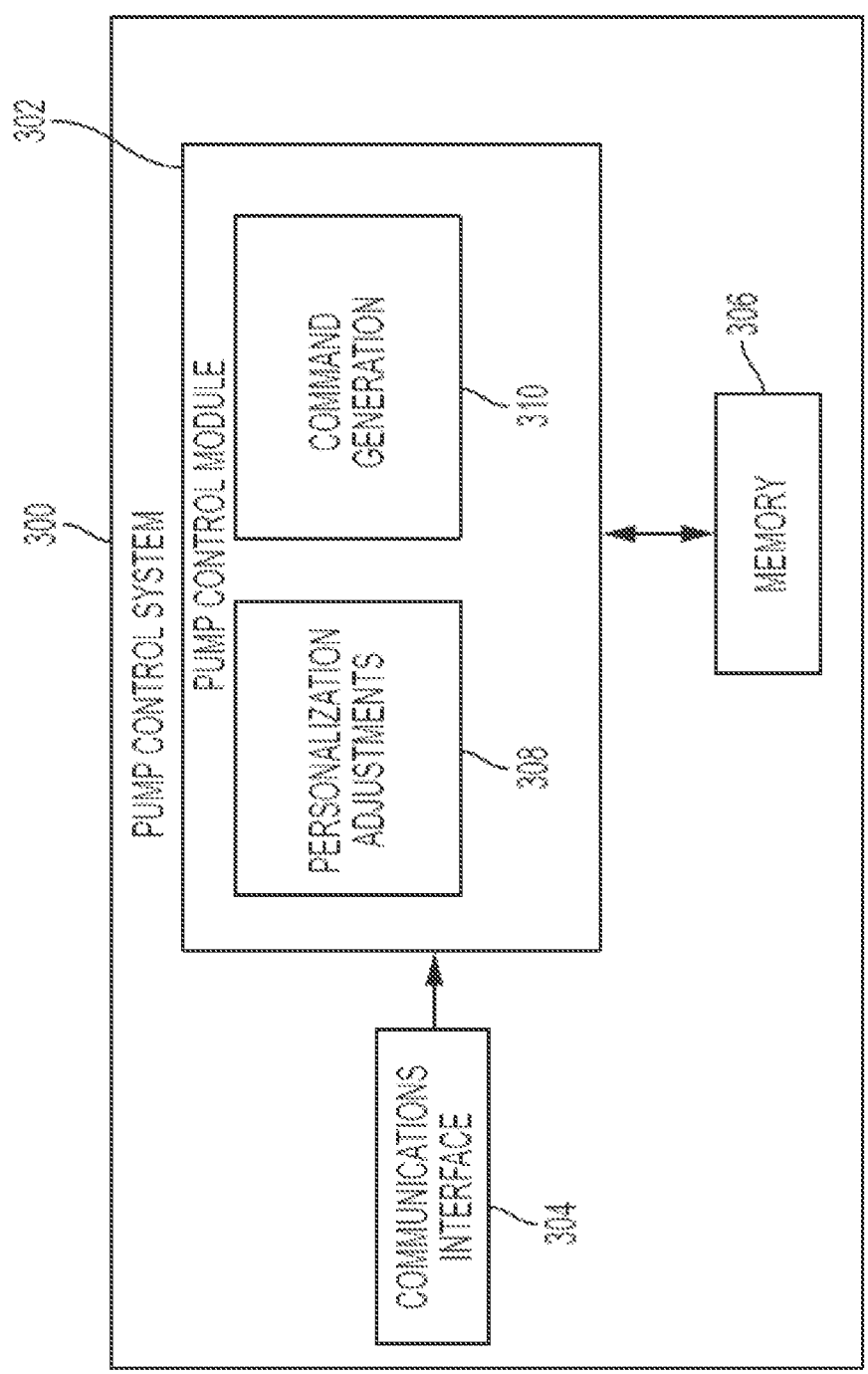
FIG. 3 is a block diagram of an exemplary pump control system suitable for use in the infusion device in the control system of FIG. 2 in one or more embodiments.

FIG. 3 depicts an exemplary embodiment of a pump control system 300 suitable for use as the pump control system 220 in FIG. 2 in accordance with one or more embodiments. The illustrated pump control system 300 includes, without limitation, a pump control module 302, a communications interface 304, and a data storage element (or memory) 306. The pump control module 302 is coupled to the communications interface 304 and the memory 306, and the pump control module 302 is suitably configured to support the operations, tasks, and/or processes described herein. In various embodiments, the pump control module 302 is also coupled to one or more user interface elements (e.g., user interface 240) for receiving user inputs (e.g., target glucose values or other glucose thresholds) and providing notifications, alerts, or other therapy information to the patient.

The communications interface 304 generally represents the hardware, circuitry, logic, firmware and/or other components of the pump control system 300 that are coupled to the pump control module 302 and configured to support communications between the pump control system 300 and the various sensing arrangements 204, 206, 208. In this regard, the communications interface 304 may include or otherwise be coupled to one or more transceiver modules capable of supporting wireless communications between the pump control system 220, 300 and the sensing arrangement(s) 204, 206, 208. For example, the communications interface 304 may be utilized to receive sensor measurement values or other measurement data from each sensing arrangement 204, 206, 208 in a control system 200. In other embodiments, the communications interface 304 may be configured to support wired communications to/from the sensing arrangement(s) 204, 206, 208. In various embodiments, the communications interface 304 may also support communications with another electronic device (e.g., CCD 106 and/or computer 108) in an infusion system (e.g., to upload sensor measurement values to a server or other computing device, receive control information from a server or other computing device, and the like).

The pump control module 302 generally represents the hardware, circuitry, logic, firmware and/or other component of the pump control system 300 that is coupled to the communications interface 304 and configured to determine dosage commands for operating the motor 232 to deliver fluid to the body 201 based on measurement data received from the sensing arrangements 204, 206, 208 and perform various additional tasks, operations, functions and/or operations described herein. For example, in exemplary embodiments, pump control module 302 implements or otherwise executes a command generation application 310 that supports one or more autonomous operating modes and calculates or otherwise determines dosage commands for operating the motor 232 of the infusion device 202 in an autonomous operating mode based at least in part on a current measurement value for a condition in the body 201 of the patient. For example, in a closed-loop operating mode, the command generation application 310 may determine a dosage command for operating the motor 232 to deliver insulin to the body 201 of the patient based at least in part on the current glucose measurement value most recently received from the sensing arrangement 204 to regulate the patient's blood glucose level to a target reference glucose value. Additionally, the command generation application 310 may generate dosage commands for boluses that are manually-initiated or otherwise instructed by a patient via a user interface element.

In exemplary embodiments, the pump control module 302 also implements or otherwise executes a personalization application 308 that is cooperatively configured to interact with the command generation application 310 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 308 may adjust or otherwise modify values for one or more parameters utilized by the command generation application 310 when determining dosage commands, for example, by modifying a parameter value at a register or location in memory 306 referenced by the command generation application 310. In yet other embodiments, the personalization application 308 may predict meals or other events or activities that are likely to be engaged in by the patient and output or otherwise provide an indication of the predicted patient behavior, which, in turn, may then be utilized to adjust the manner in which dosage commands are generated to regulate glucose in a manner that accounts for the patient's predicted behavior in a personalized manner. In some embodiments, the personalization application 308 may support automatically performing personalized adjustments of control parameters utilized by the command generation application 310.

Still referring to FIG. 3, depending on the embodiment, the pump control module 302 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 302, or in any practical combination thereof. In exemplary embodiments, the pump control module 302 includes or otherwise accesses the data storage element or memory 306, which may be realized using any sort of non-transitory computer-readable medium capable of storing programming instructions for execution by the pump control module 302. The computer-executable programming instructions, when read and executed by the pump control module 302, cause the pump control module 302 to implement or otherwise generate the applications 308, 310 and perform tasks, operations, functions, and processes described herein.

It should be understood that FIG. 3 is a simplified representation of a pump control system 300 for purposes of explanation and is not intended to limit the subject matter described herein in any way. For example, in some embodiments, the features and/or functionality of the motor control module 212 may be implemented by or otherwise integrated into the pump control system 300 and/or the pump control module 302, for example, by the command generation application 310 converting the dosage command into a corresponding motor command, in which case, the separate motor control module 212 may be absent from an embodiment of the infusion device 202.

Figure 4:
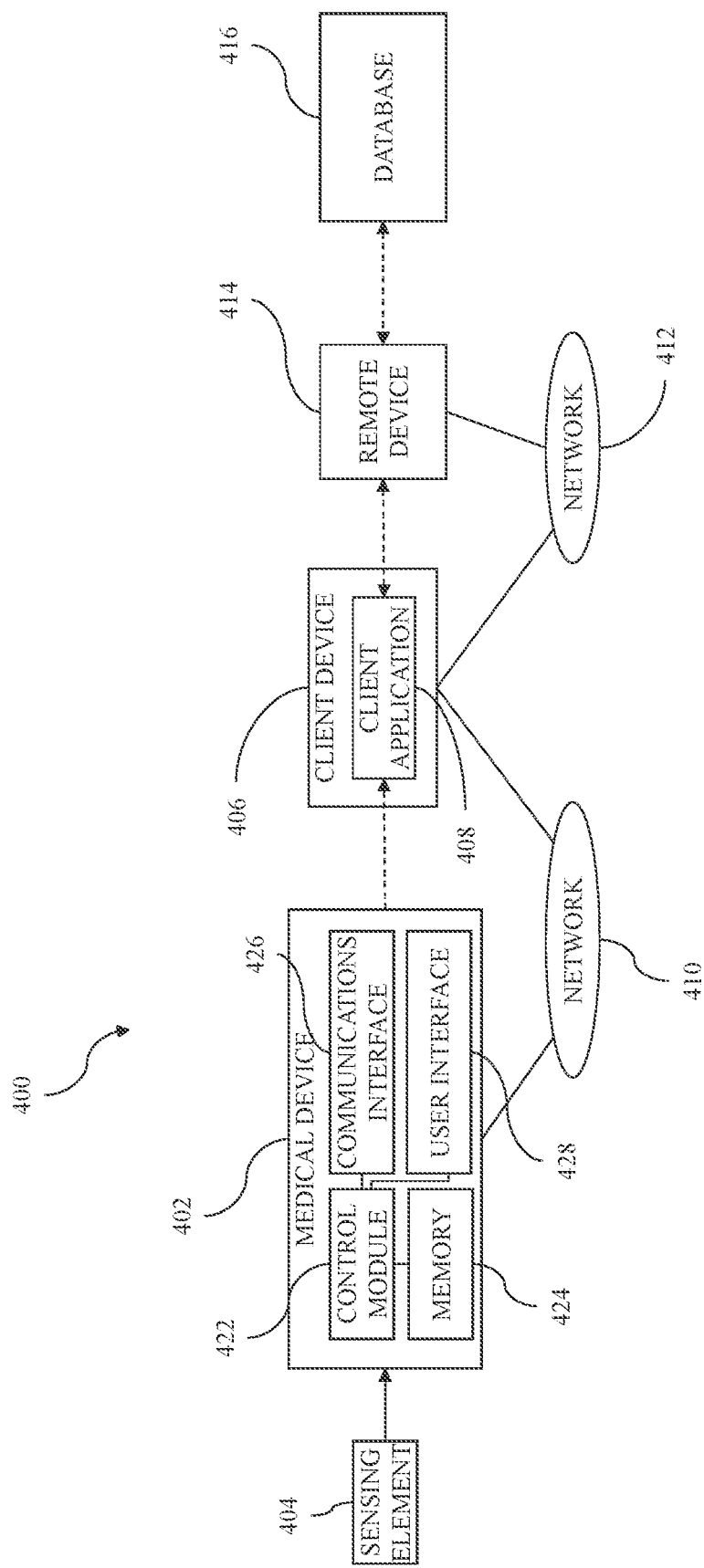
FIG. 4 is a block diagram of an exemplary patient monitoring system.

FIG. 4 depicts an exemplary embodiment of a patient monitoring system 400. The patient monitoring system 400 includes a medical device 402 that is communicatively coupled to a sensing element 404 that is inserted into the body of a patient or otherwise worn by the patient to obtain measurement data indicative of a physiological condition in the body of the patient, such as a sensed glucose level. The medical device 402 is communicatively coupled to a client device 406 via a communications network 410, with the client device 406 being communicatively coupled to a remote device 414 via another communications network 412. In this regard, the client device 406 may function as an intermediary for uploading or otherwise providing measurement data from the medical device 402 to the remote device 414. It should be appreciated that FIG. 4 depicts a simplified representation of a patient monitoring system 400 for purposes of explanation and is not intended to limit the subject matter described herein in any way.

In exemplary embodiments, the client device 406 is realized as a mobile phone, a smartphone, a tablet computer, or other similar mobile electronic device; however, in other embodiments, the client device 406 may be realized as any sort of electronic device capable of communicating with the medical device 402 via network 410, such as a laptop or notebook computer, a desktop computer, or the like. In exemplary embodiments, the network 410 is realized as a Bluetooth network, a ZigBee network, or another suitable personal area network. That said, in other embodiments, the network 410 could be realized as a wireless ad hoc network, a wireless local area network (WLAN), or local area network (LAN). The client device 406 includes or is coupled to a display device, such as a monitor, screen, or another conventional electronic display, capable of graphically presenting data and/or information pertaining to the physiological condition of the patient. The client device 406 also includes or is otherwise associated with a user input device, such as a keyboard, a mouse, a touchscreen, or the like, capable of receiving input data and/or other information from the user of the client device 406.

In some embodiments, a user, such as the patient, the patient's doctor or another healthcare provider, or the like, manipulates the client device 406 to execute a client application 408 that supports communicating with the medical device 402 via the network 410. In this regard, the client application 408 supports establishing a communications session with the medical device 402 on the network 410 and receiving data and/or information from the medical device 402 via the communications session. The medical device 402 may similarly execute or otherwise implement a corresponding application or process that supports establishing the communications session with the client application 408. The client application 408 generally represents a software module or another feature that is generated or otherwise implemented by the client device 406 to support the processes described herein. Accordingly, the client device 406 generally includes a processing system and a data storage element (or memory) capable of storing programming instructions for execution by the processing system, that, when read and executed, cause processing system to create, generate, or otherwise facilitate the client application 408 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 406 and the medical device 402 establish an association (or pairing) with one another over the network 410 to support subsequently establishing a point-to-point communications session between the medical device 402 and the client device 406 via the network 410. For example, in accordance with one embodiment, the network 410 is realized as a Bluetooth network, wherein the medical device 402 and the client device 406 are paired with one another (e.g., by obtaining and storing network identification information for one another) by performing a discovery procedure or another suitable pairing procedure. The pairing information obtained during the discovery procedure allows either of the medical device 402 or the client device 406 to initiate the establishment of a secure communications session via the network 410.

In one or more exemplary embodiments, the client application 408 is also configured to store or otherwise maintain an address and/or other identification information for the remote device 414 on the second network 412. In this regard, the second network 412 may be physically and/or logically distinct from the network 410, such as, for example, the Internet, a cellular network, a wide area network (WAN), or the like. The remote device 414 generally represents a server or other computing device configured to receive and analyze or otherwise monitor measurement data, event log data, and potentially other information obtained for the patient associated with the medical device 402. In exemplary embodiments, the remote device 414 is coupled to a database 416 configured to store or otherwise maintain data associated with individual patients. In practice, the remote device 414 may reside at a location that is physically distinct and/or separate from the medical device 402 and the client device 406, such as, for example, at a facility that is owned and/or operated by or otherwise affiliated with a manufacturer of the medical device 402. For purposes of explanation, but without limitation, the remote device 414 may alternatively be referred to herein as a server.

It should be noted that in some embodiments, some or all of the functionality and processing intelligence of the remote computing device 414 can reside at the medical device 402 and/or at other components or computing devices that are compatible with the patient monitoring system 400. In other words, the patient monitoring system 400 need not rely on a network-based or a cloud-based server arrangement as depicted in FIG. 4, although such a deployment might be the most efficient and economical implementation. These and other alternative arrangements are contemplated by this disclosure. To this end, some embodiments of the system 400 may include additional devices and components that serve as data sources, data processing units, and/or recommendation delivery mechanisms. For example, the system 400 may include any or all of the following elements, without limitation: computer devices or systems; patient monitors; healthcare provider systems; data communication devices; and the like.

Still referring to FIG. 4, the sensing element 404 generally represents the component of the patient monitoring system 400 that is configured to generate, produce, or otherwise output one or more electrical signals indicative of a physiological condition that is sensed, measured, or otherwise quantified by the sensing element 404. In this regard, the physiological condition of a patient influences a characteristic of the electrical signal output by the sensing element 404, such that the characteristic of the output signal corresponds to or is otherwise correlative to the physiological condition that the sensing element 404 is sensitive to. In exemplary embodiments, the sensing element 404 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 404.

The medical device 402 generally represents the component of the patient monitoring system 400 that is communicatively coupled to the output of the sensing element 404 to receive or otherwise obtain the measurement data samples from the sensing element 404 (e.g., the measured glucose and characteristic impedance values), store or otherwise maintain the measurement data samples, and upload or otherwise transmit the measurement data to the server 414 via the client device 406. In one or more embodiments, the medical device 402 is realized as an infusion device 102, 202 configured to deliver a fluid, such as insulin, to the body of the patient. That said, in other embodiments, the medical device 402 could be a standalone sensing or monitoring device separate and independent from an infusion device (e.g., sensing arrangement 104, 204), such as, for example, a continuous glucose monitor (CGM), an interstitial glucose sensing arrangement, or similar device. It should be noted that although FIG. 4 depicts the medical device 402 and the sensing element 404 as separate components, in practice, the medical device 402 and the sensing element 404 may be integrated or otherwise combined to provide a unitary device that can be worn by the patient.

In exemplary embodiments, the medical device 402 includes a control module 422, a data storage element 424 (or memory), a communications interface 426, and a user interface 428. The user interface 428 generally represents the input user interface element(s) and/or output user interface element(s) associated with the medical device 402 (e.g., one or more user interface elements 240). The control module 422 generally represents the hardware, circuitry, logic, firmware and/or other component(s) of the medical device 402 that is coupled to the sensing element 404 to receive the electrical signals output by the sensing element 404 and perform or otherwise support various additional tasks, operations, functions and/or processes described herein. Depending on the embodiment, the control module 422 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 422 includes an analog-to-digital converter (ADC) or another similar sampling arrangement that samples or otherwise converts an output electrical signal received from the sensing element 404 into corresponding digital measurement data value. In other embodiments, the sensing element 404 may incorporate an ADC and output a digital measurement value.

The communications interface 426 generally represents the hardware, circuitry, logic, firmware and/or other components of the medical device 402 that are coupled to the control module 422 for outputting data and/or information from/to the medical device 402 to/from the client device 406. For example, the communications interface 426 may include or otherwise be coupled to one or more transceiver modules capable of supporting wireless communications between the medical device 402 and the client device 406. In exemplary embodiments, the communications interface 426 is realized as a Bluetooth transceiver or adapter configured to support Bluetooth Low Energy (BLE) communications.

In exemplary embodiments, the remote device 414 receives, from the client device 406, measurement data values associated with a particular patient (e.g., sensor glucose measurements, acceleration measurements, and the like) that were obtained using the sensing element 404, and the remote device 414 stores or otherwise maintains the historical measurement data in the database 416 in association with the patient (e.g., using one or more unique patient identifiers). Additionally, the remote device 414 may also receive, from or via the client device 406, meal data or other event log data that may be input or otherwise provided by the patient (e.g., via client application 408) and store or otherwise maintain historical meal data and other historical event or activity data associated with the patient in the database 416. In this regard, the meal data include, for example, a time or timestamp associated with a particular meal event, a meal type or other information indicative of the content or nutritional characteristics of the meal, and an indication of the size associated with the meal. In exemplary embodiments, the remote device 414 also receives historical fluid delivery data corresponding to basal or bolus dosages of fluid delivered to the patient by an infusion device 102, 202. For example, the client application 408 may communicate with an infusion device 102, 202 to obtain insulin delivery dosage amounts and corresponding timestamps from the infusion device 102, 202, and then upload the insulin delivery data to the remote device 414 for storage in association with the particular patient. The remote device 414 may also receive geolocation data and potentially other contextual data associated with a device 402, 406 from the client device 406 and/or client application 408, and store or otherwise maintain the historical operational context data in association with the particular patient. In this regard, one or more of the devices 402, 406 may include a global positioning system (GPS) receiver or similar modules, components or circuitry capable of outputting or otherwise providing data characterizing the geographic location of the respective device 402, 406 in real-time.

Personalized Bolus Process

In exemplary embodiments, an infusion device (or a control system associated therewith) is capable of determining a bolus amount in a personalized manner that reduces the burden associated with carbohydrate counting by allowing the patient to qualitatively define the size of a meal, with the qualitative user input being converted into a corresponding quantitative representation of the qualitative meal size based on the patient's historical data. The quantitative representation is then utilized to determine a meal bolus dosage without requiring carbohydrate counting or other manual calculations or estimations. In exemplary embodiments, a patient's historical meal events are clustered into different groups or subsets, alternatively referred to herein as clusters, with each respective group or subset being associated with a different qualitative meal size. Thereafter, for an input qualitative meal size, a patient-specific carbohydrate amount that is representative of the cluster of the patient's historical meal events associated with the input qualitative meal size is identified and utilized to determine a bolus dosage for the input qualitative meal size. In exemplary embodiments, the carbohydrate amount associated with the centroid of the qualitative meal size cluster is utilized as the patient-specific carbohydrate amount associated with the input qualitative meal size.

Figure 5:
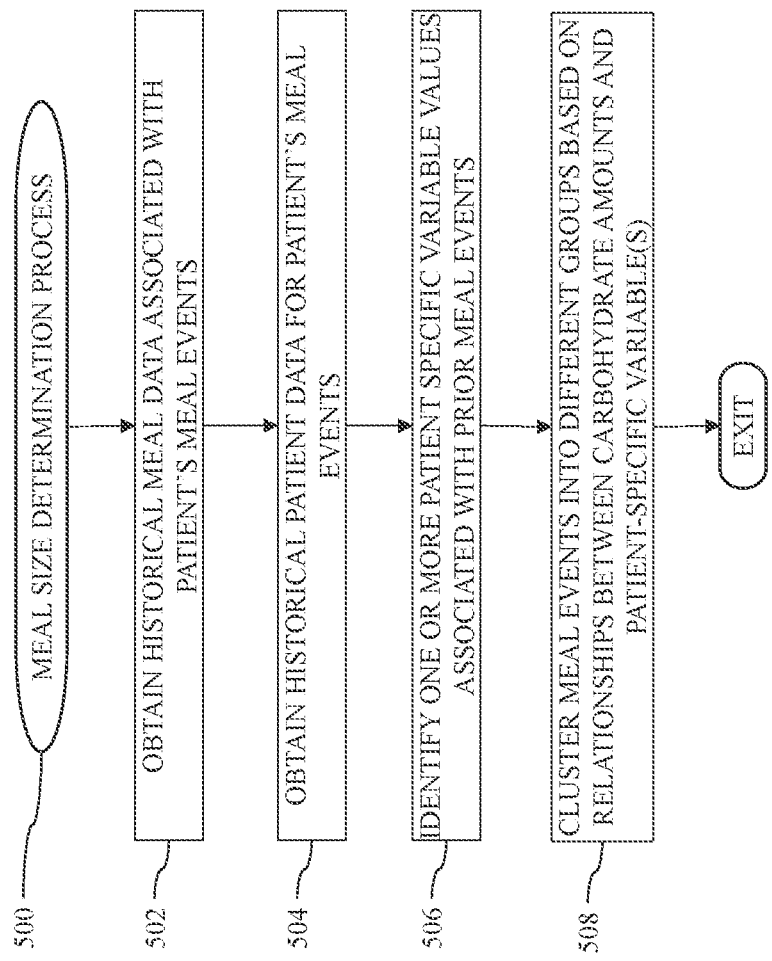
FIG. 5 is a flow diagram of an exemplary meal size determination process suitable implementation in connection with an infusion device in one or more exemplary embodiments.

FIG. 5 depicts an exemplary embodiment of a meal size determination process 500 that may be performed to assign the patient's historical meal events to different qualitative meal sizes, and thereby determine a representative carbohydrate amount or other quantitative attributes associated with a respective qualitative meal size based on its associated subset of historical meal events. The various tasks performed in connection with the meal size determination process 500 may be performed by hardware, firmware, software executed by processing circuitry, or any combination thereof. For illustrative purposes, the following description refers to elements mentioned above in connection with FIGS. 1-4. In practice, portions of the meal size determination process 500 may be performed by different elements of an infusion system, such as, for example, an infusion device 102, 202, 402, a client computing device 106, 406, a remote computing device 108, 414, and/or a pump control system 220, 300. It should be appreciated that the meal size determination process 500 may include any number of additional or alternative tasks, the tasks need not be performed in the illustrated order and/or the tasks may be performed concurrently, and/or the meal size determination process 500 may be incorporated into a more comprehensive procedure or process having additional functionality not described in detail herein. Moreover, one or more of the tasks shown and described in the context of FIG. 5 could be omitted from a practical embodiment of the meal size determination process 500 as long as the intended overall functionality remains intact.

In exemplary embodiments, meal size determination process 500 is performed once sufficient historical meal data and corresponding patient measurement data has been obtained and stored in the database 416. For example, for an initial setup monitoring period, the patient may estimate or input meal sizes when logging meal events while also manually interacting with a bolus wizard or other feature of the infusion device 102, 202, 402 or a client application 408 on the client device 106, 406 to configure and administer boluses for the contemporaneous meal events. In this regard, during the initial setup monitoring period, the patient may perform carbohydrate counting and provide indication of the estimated carbohydrate amounts associated with those meals. Once the elapsed duration of the monitoring period is greater than a threshold setup period (e.g., 2 weeks) or a sufficient number of meal events have been logged or otherwise documented, the remote server 414 may perform the meal size determination process 500 to categorize or otherwise assign prior meal events to different qualitative meal size groups and determine corresponding quantitative attributes representative of the different qualitative meal size groups.

The meal size determination process 500 begins by receiving or otherwise obtaining historical meal data associated with a patient's prior meal events along with historical measurement data and/or other patient data pertaining to those prior meal events (tasks 502, 504). In this regard, the meal size determination process 500 obtains (e.g., from database 416) the timestamps or other indicia associated with the patient's prior meal events and the carbohydrate amounts associated with the patient's prior meal events. The meal size determination process 500 also obtains (e.g., from database 416) the patient's historical glucose measurement data and potentially other historical data (e.g., historical insulin delivery data) contemporaneous or concurrent to those prior meal events (e.g., using the timestamps associated with the prior meal events). Depending on the embodiment, carbohydrate amounts associated with the patient's prior meal events may be those carbohydrate amounts that were input or otherwise provided by the patient at the time of the meal (e.g., in connection with administering a meal bolus), or the carbohydrate amounts may be retrospectively determined based on the relationships between the patient's historical glucose measurement data and insulin delivery data around the prior meal events. In this regard, in some embodiments, prior meal events may be retrospectively detected or otherwise identified from analysis of the patient's historical data.

The meal size determination process 500 continues by identifying or otherwise obtaining patient-specific values for one or more variables associated with the prior meal events (task 506). In this regard, the patient-specific values represent the quantitative state of the variable(s) contemporaneous to, concurrent to, or otherwise temporally associated with the prior meal events, which, in turn, are utilized to add dimensionality to the data associated with the prior meal events for purposes of clustering the prior meal events, as described in greater detail below. For example, patient-specific carbohydrate ratio values associated with prior meal events may be determined based on the relationship between the historical meal data associated with the prior meal events and the corresponding historical glucose measurement and insulin delivery data. In exemplary embodiments, for each meal event, a value representing the postprandial change in sensor glucose measurement value per carbohydrate ($\Delta SG_{pp}$/Carbs) is determined based on the relationship between the patient's historical sensor glucose measurement data and the amount of carbohydrates associated with each respective meal event using the timestamp associated with the respective meal event. For example, the inflection point corresponding to the maximum sensor glucose measurement value after a meal (alternatively referred to herein as the postprandial peak sensor glucose measurement value) may be identified based on the rate of change in the sensor glucose measurement values at or after the timestamp associated with a respective meal event (e.g., when the sensor glucose measurement values stop increasing). The postprandial change in the patient's sensor glucose ($\Delta SG_{pp}$) may be determined by subtracting the sensor glucose measurement value corresponding to the start of the meal event (e.g., the value having a timestamp nearest to the timestamp associated with the respective meal event) from the postprandial peak sensor glucose measurement value. In this regard, based on the initial sensor glucose measurement value at or before the timestamp associated with the meal event and the peak sensor glucose measurement value following the meal event, the change in postprandial sensor glucose value between the postprandial peak sensor glucose measurement value and the initial sensor glucose measurement value (e.g., $\Delta SG_{pp}$) may be determined for the respective meal event and divided by the amount of carbohydrates associated with the respective meal event to arrive at the net change in postprandial sensor glucose change per carbohydrate ($\Delta SG_{pp}$/Carbs) associated with that meal event.

Still referring to FIG. 5, the meal size determination process 500 utilizes the relationship between the patient-specific variable values and the carbohydrate amounts associated with the prior meal events to cluster the prior meal events into different subsets or groups corresponding to different qualitative meal sizes (task 508). In this regard, each of the prior meal events is assigned to a qualitative meal size cluster group based on the degree of similarity relative to other prior meal events assigned to that qualitative meal size cluster group. The qualitative meal size cluster groups are unique and mutually exclusive with respect to one another, such that each prior meal event is only assigned to one cluster group. In exemplary embodiments, a k-means clustering technique is utilized to divide the prior meal events into a predefined number of qualitative meal sizes based on their associated carbohydrate amounts. For example, k-means clustering may be utilized to cluster the patient's prior meal events into 3 qualitative meal sizes (e.g., small, medium, large), or any number of additional qualitative meal sizes (e.g., snack, extra-large, etc.) as desired and described in greater detail below. That said, it should be noted that the subject matter described herein is not limited to any particular type of clustering technique, any particular number of variables or features analyzed for the purposes of clustering, and/or any particular number of cluster groups.

Figure 6:
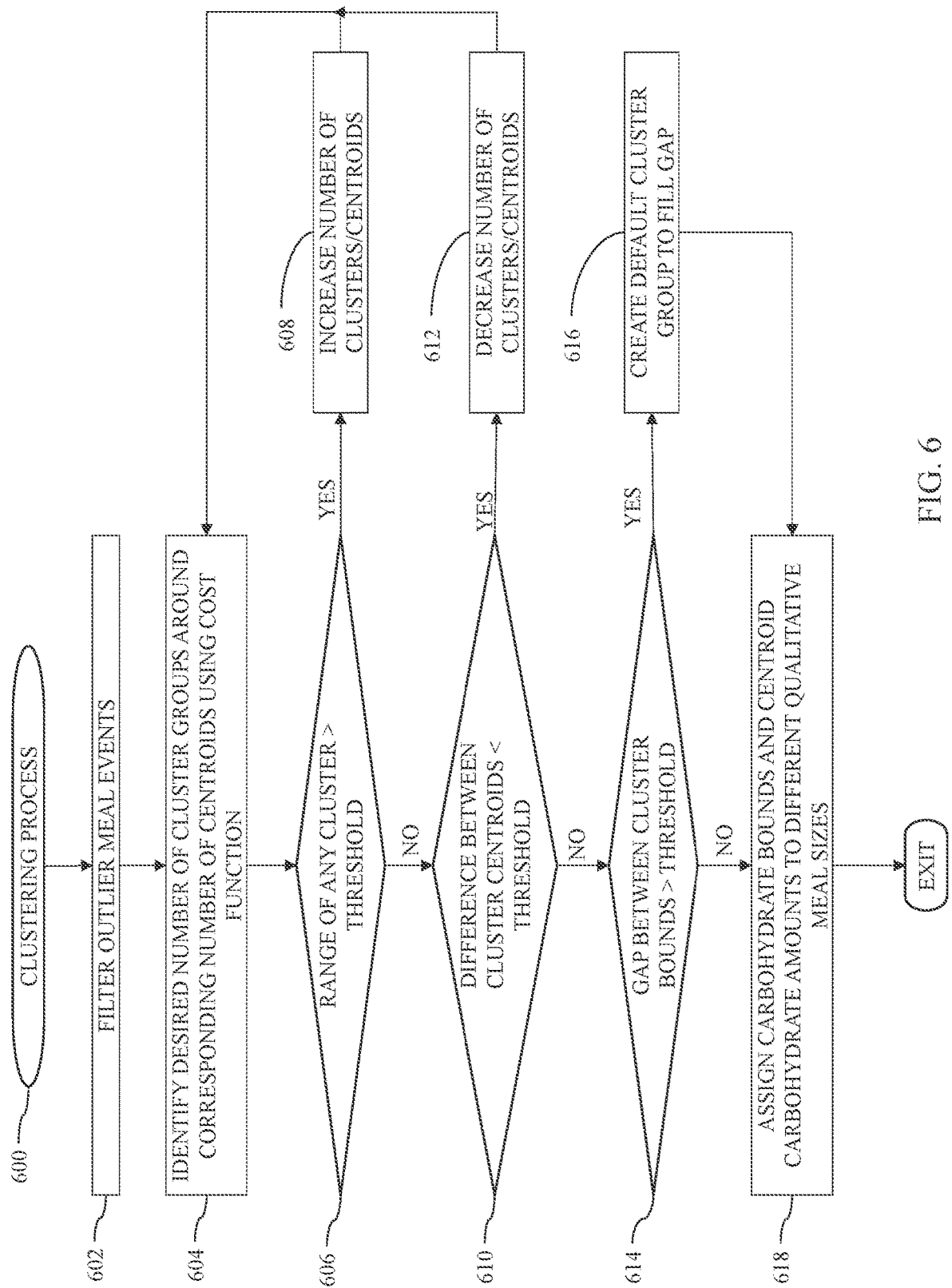
FIG. 6 is a flow diagram of an exemplary clustering process suitable implementation in connection with the meal size determination process of FIG. 5 in one or more exemplary embodiments.

FIG. 6 depicts an exemplary embodiment of a clustering process 600 that may be performed in connection with the meal size determination process 500 to assign the patient's historical meal events to different qualitative meal size clusters. The various tasks performed in connection with the clustering process 600 may be performed by hardware, firmware, software executed by processing circuitry, or any combination thereof. For illustrative purposes, the following description refers to elements mentioned above in connection with FIGS. 1-4. In practice, portions of the clustering process 600 may be performed by different elements of an infusion system, such as, for example, an infusion device 102, 202, 402, a client computing device 106, 406, a remote computing device 108, 414, and/or a pump control system 220, 300. It should be appreciated that the clustering process 600 may include any number of additional or alternative tasks, the tasks need not be performed in the illustrated order and/or the tasks may be performed concurrently, and/or the clustering process 600 may be incorporated into a more comprehensive procedure or process having additional functionality not described in detail herein. Moreover, one or more of the tasks shown and described in the context of FIG. 6 could be omitted from a practical embodiment of the clustering process 600 as long as the intended overall functionality remains intact.

The illustrated clustering process 600 begins by filtering or otherwise excluding outlier meal events from consideration prior to dividing the patient's prior meal events into the desired number of cluster groups (task 602). For example, the clustering process 600 may remove from consideration any prior meal events that have an associated carbohydrate amount that appears to be anomalous or otherwise deviates from the other prior meal events by more than a threshold. Additionally, the clustering process 600 may remove from consideration any prior meal events that have associated patient-specific variable values (e.g., from task 506) that appear to be anomalous or otherwise deviate from those associated with other prior meal events by more than a threshold.

After removing outliers, the clustering process 600 continues by initially identifying or otherwise determining the desired number of cluster groups around a corresponding number of centroids using a cost function (task 604). For example, in one embodiment, for the k-means clustering technique, the desired number of potential centroids are initially identified, with prior meal event being assigned to its nearest centroid in accordance with a cost function that minimizes the Euclidean distance between the prior meal event data points and the centroid of their respective cluster. The k-means clustering technique then redetermines updated centroids corresponding to the mean of the subset of prior meal event data points assigned to the respective cluster. The prior meal events are then reassigned to the nearest updated centroid in accordance with a cost function that minimizes the Euclidean distance between the prior meal event data points and the updated centroid of the respective clusters. In this manner, the clustering process 600 iteratively determines centroids and corresponding cluster groups to progressively minimize the cost in accordance with the cost function until achieving a minimum cost or performing a desired number of iterations.

In exemplary embodiments, the clustering process 600 verifies or otherwise confirms that the range between the minimum and maximum carbohydrate amounts for prior meal events assigned to each respective cluster is not greater than a threshold value (task 606). In this manner, the clustering process 600 attempts to ensure that any cluster group is not so large as to detrimentally impact the efficacy or safety of any resulting bolus, as described in greater detail below. When the range between the lower and upper carbohydrate bounds for a qualitative meal size cluster is greater than the threshold, the clustering process 600 incrementally increases the number of cluster groups to add another qualitative meal size cluster group (task 608) and then identifies the updated number of cluster groups from within the prior meal events (task 604). For example, if the range between the carbohydrate amounts associated with any two prior meal events assigned to a respective qualitative meal size cluster is greater than 30 grams, the clustering process 600 may incrementally increase the number of qualitative meal size cluster groups until the range between the lower and upper carbohydrate bounds for each of the qualitative meal size clusters is less than 30 grams.

In exemplary embodiments, the clustering process 600 also verifies or otherwise confirms the minimum difference between the carbohydrate amounts associated with the centroids of neighboring cluster groups is greater than a threshold (task 610). In this manner, the clustering process 600 attempts to ensure that there are not excess cluster groups for an individual patient to simplify options for selecting or inputting the meal size. When the minimum difference between the carbohydrate amounts associated with the centroids of neighboring cluster groups is less than the threshold, the clustering process 600 incrementally decreases the number of cluster groups to remove a qualitative meal size cluster group (task 612) and then identifies the updated number of cluster groups from within the prior meal events (task 604). For example, if the minimum difference between the centroid carbohydrate amounts for two qualitative meal size cluster groups is less than 10 grams, the clustering process 600 may incrementally decrease the number of qualitative meal size cluster groups. In this regard, the number of qualitative meal size cluster groups may vary from patient to patient depending on each patient's unique distribution of carbohydrate amounts across their prior meal events.

Still referring to FIG. 6, in exemplary embodiments, the clustering process 600 also verifies or otherwise confirms that the difference between the adjacent bounds of neighboring cluster groups is less than a threshold (task 614). In this regard, when the difference between the upper carbohydrate bounds associated with one qualitative meal size cluster group and the lower carbohydrate bounds associated with the next larger qualitative meal size cluster group is greater than a threshold, the clustering process 600 automatically creates a default cluster group having carbohydrate bounds that span the range between the two qualitative meal size cluster groups. In this manner, the clustering process 600 provides an alternative qualitative meal size for the patient to select to account for prospective meal events in the future that would not otherwise align with the qualitative meal size cluster groups identified based on the patient's prior meal events. In exemplary embodiments, the centroid carbohydrate amount for the default cluster group is determined by adding one third of the range between the lower and upper carbohydrate boundaries for the default cluster group to the lower carbohydrate boundary. In some embodiments, the clustering process 600 may repeat the steps of reassigning prior meal events to different cluster groups using the default cluster group centroid carbohydrate amount along with the previously determined cluster group centroids (e.g., task 604).

After the patient's prior meal events have been assigned to different qualitative meal size clusters that have the desired carbohydrate range (e.g., task 606) and the desired differentiation between clusters (e.g., task 610) without excessive gaps between clusters (e.g., task 614), the clustering process 600 assigns carbohydrate bounds and a centroid carbohydrate amount to each of the qualitative meal size clusters (task 618). In exemplary embodiments, the clustering process 600 identifies the carbohydrate amount that is associated with the prior meal event of the qualitative meal size cluster having the minimum carbohydrate amount associated therewith as the lower carbohydrate boundary for the qualitative meal size cluster. Similarly, the clustering process 600 identifies the carbohydrate amount that is associated with the prior meal event of the qualitative meal size cluster having the maximum carbohydrate amount associated therewith as the upper carbohydrate boundary for the qualitative meal size cluster. To assign a centroid carbohydrate amount to the qualitative meal size cluster, the clustering process 600 identifies, calculates, or otherwise determines a centroid based on the subset of prior meal event data points associated with the qualitative meal size cluster, and then identifies the carbohydrate amount associated with the centroid as the centroid carbohydrate amount for the qualitative meal size cluster. In this regard, the centroid carbohydrate amount may be different from the mean, median, or average carbohydrate amount for the prior meal events assigned to a respective qualitative meal size cluster. It should be noted that in some embodiments, the smallest and/or largest qualitative meal size clusters may be open-ended and assigned only one carbohydrate boundary, for example, due to insufficient data. For example, the largest qualitative meal size cluster may be assigned only a lower carbohydrate boundary, while the smallest qualitative meal size cluster may be assigned only an upper carbohydrate boundary.

Figure 7:
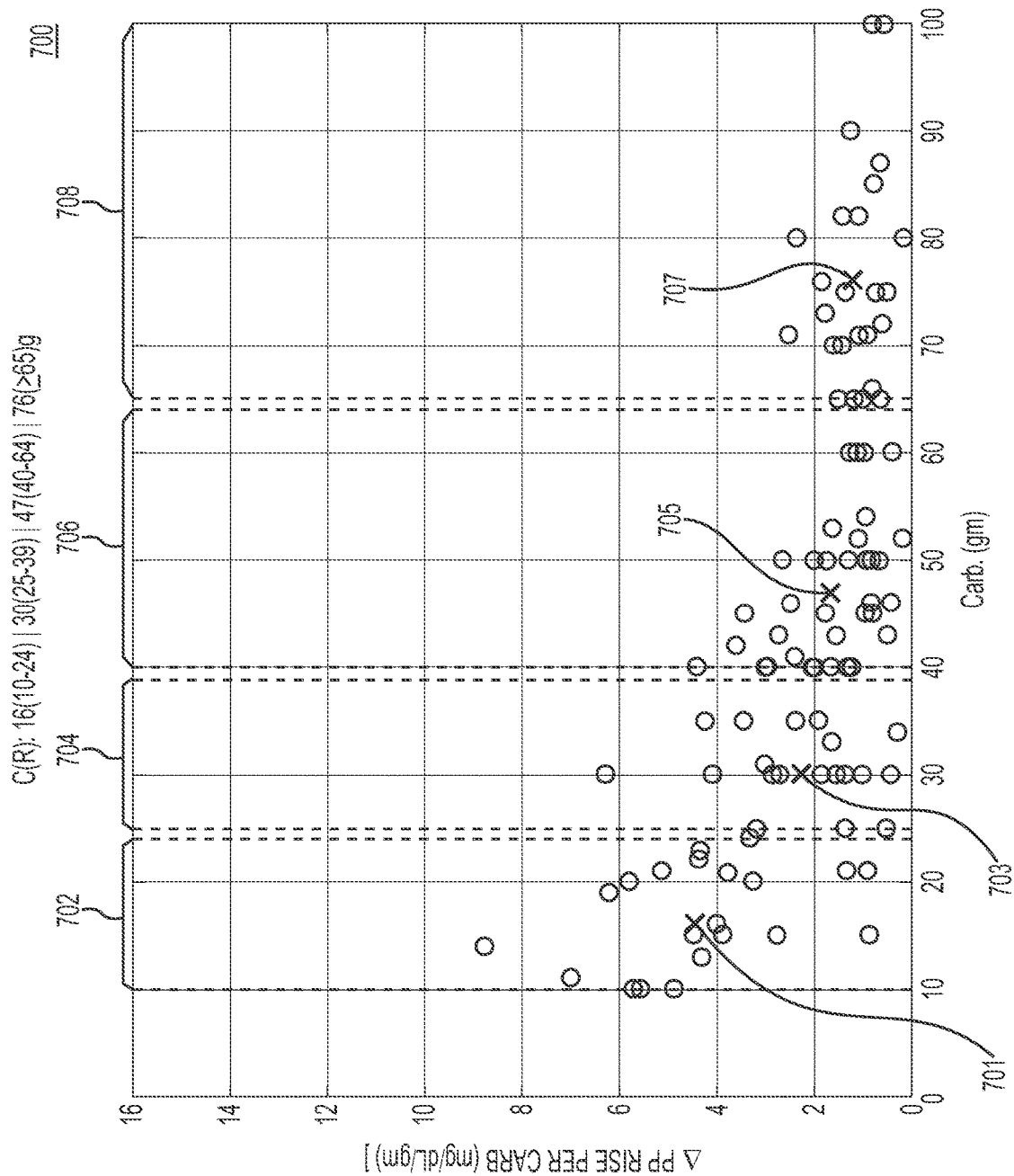
FIGS. 7-8 depict graphs of meal event data suitable for clustering into qualitative meal size groups in connection with the clustering process of FIG. 6 in one or more exemplary embodiments.

FIG. 7 depicts a graph 700 of a prior meal events assigned into different qualitative meal size clusters 702, 704, 706, 708 having different centroids 701, 703, 705, 707 associated therewith based the relationship between the carbohydrate amounts associated with the prior meal events and the postprandial sensor glucose change per unit carbohydrate ($\Delta SG_{pp}$/Carbs) in accordance with the clustering process 600 of FIG. 6. For example, the remote server 414 may obtain the historical data associated with the patient's prior meal events from the database 416 and perform the clustering process 600 on the obtained data to identify different qualitative meal size cluster groups and corresponding quantitative carbohydrate amounts, which, in turn may be pushed or otherwise provided to another device 402, 406 for purposes of bolusing, as described in greater detail below in the context of FIG. 9.

In the illustrated embodiment of FIG. 7, the prior meal events are divided into a lowest qualitative meal size cluster 702 having a lower carbohydrate boundary of 10 grams, an upper carbohydrate boundary of 24 grams, and a centroid carbohydrate amount of 16 grams, a next larger qualitative meal size cluster 704 having a lower carbohydrate boundary of 25 grams, an upper carbohydrate boundary of 39 grams, and a centroid carbohydrate amount of 30 grams, a next larger qualitative meal size cluster 706 having a lower carbohydrate boundary of 40 grams, an upper carbohydrate boundary of 64 grams, and a centroid carbohydrate amount of 47 grams, and a largest qualitative meal size cluster 708 having a lower carbohydrate boundary of 65 grams and a centroid carbohydrate amount of 76 grams. Depending on the embodiment, the largest meal size cluster 708 may be assigned an upper carbohydrate boundary corresponding to the maximum carbohydrate amount from among the subset of prior meal events assigned to the cluster group (e.g., 100 grams) or be left open-ended without an assigned upper carbohydrate boundary. As illustrated, the qualitative meal size clusters 702, 704, 706, 708 are unique or otherwise mutually exclusive, such that no prior meal event is assigned to more than one cluster group.

After clustering the prior meal events in accordance with the clustering process 600, the meal size determination process 500 may assign qualitative meal sizes to the different cluster groups. For example, the lowest qualitative meal size cluster group 702 may be assigned the qualitative meal size of small, while the next larger qualitative meal size cluster group 704 is assigned the qualitative meal size of medium, the next larger qualitative meal size cluster group 706 is assigned the qualitative meal size of large, and the largest qualitative meal size cluster group 708 may be assigned the qualitative meal size of large. In this regard, the meal size determination process 500 may identify the qualitative meal sizes for assignment based on the number of cluster groups and/or the centroid carbohydrate amounts, and utilize any number or combination of logic rules to assign qualitative meal size names to cluster groups in a logical manner that would make sense to the patient. Additionally, some embodiments may allow the patient to manually define or otherwise personalize the qualitative meal size names assigned to the different cluster groups to reflect his or her personal characterization of his or her meal habits.

Figure 8:
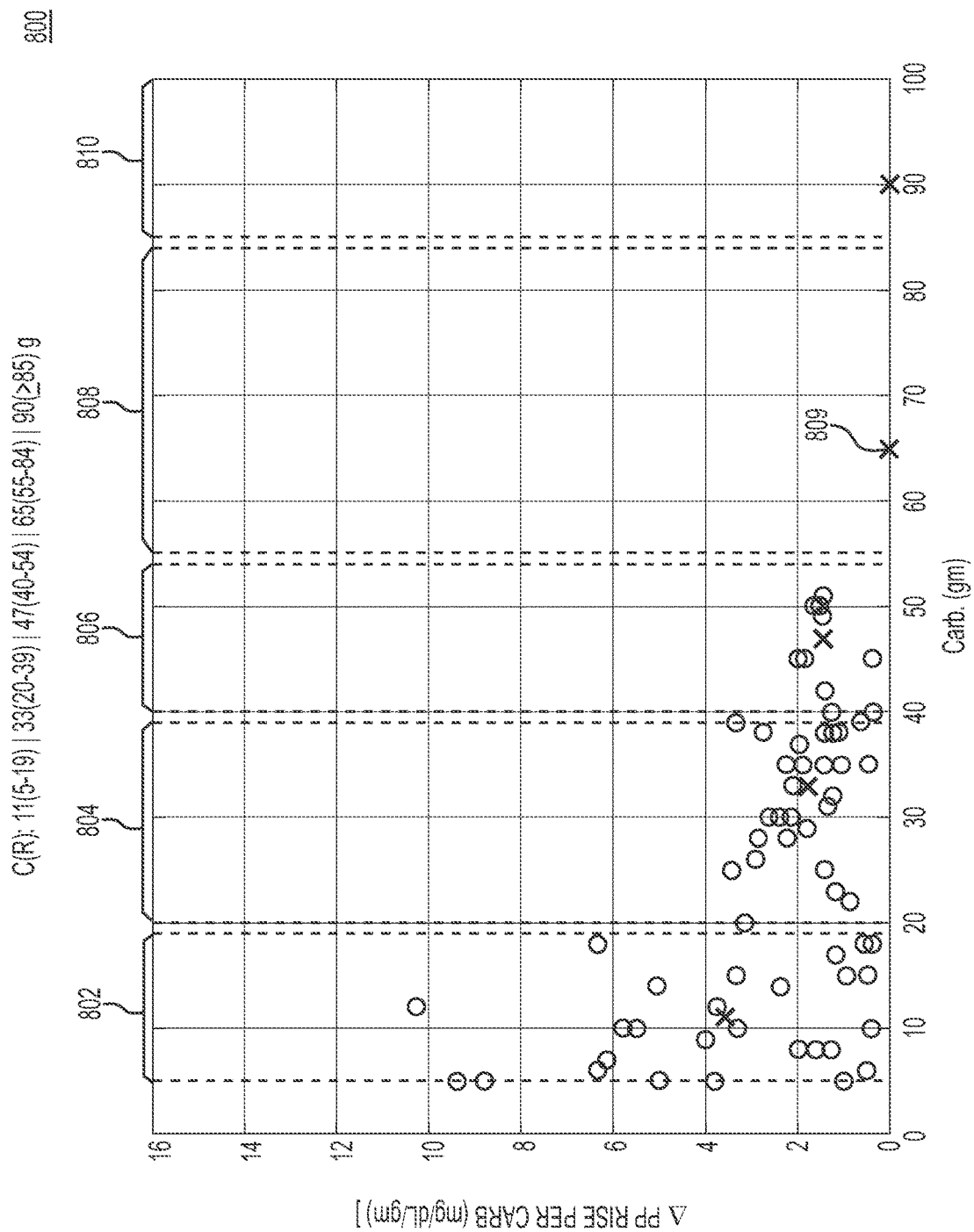

FIG. 8 depicts another graph 800 of a prior meal events assigned into different qualitative meal size clusters 802, 804, 806, 808, 810 based the relationship between the carbohydrate amounts associated with the prior meal events and the postprandial sensor glucose measurement value change per unit carbohydrate ($\Delta SG_{pp}$/Carbs) in accordance with the clustering process 600 of FIG. 6. In this regard, FIG. 8 depicts an example where an additional default cluster group 808 is introduced between an intermediate cluster group 804 (ranging from 40 grams to 54 grams with a centroid carbohydrate amount of 47 grams) and the largest qualitative meal size cluster group 810 (ranging from 85 grams to 100 grams with a centroid carbohydrate amount of 90 grams) to fill the gap between the upper carbohydrate boundary for the intermediate cluster group 804 (e.g., 54 grams) and the lower carbohydrate boundary for the largest qualitative meal size cluster group 810 (e.g., 85 grams). In exemplary embodiments, the centroid 809 of the default cluster group 808 is set as the sum of the lower carbohydrate boundary (55 grams) and one-third of the range between boundaries of the cluster group 808 to obtain a centroid carbohydrate amount of 65 grams.

Figure 9:
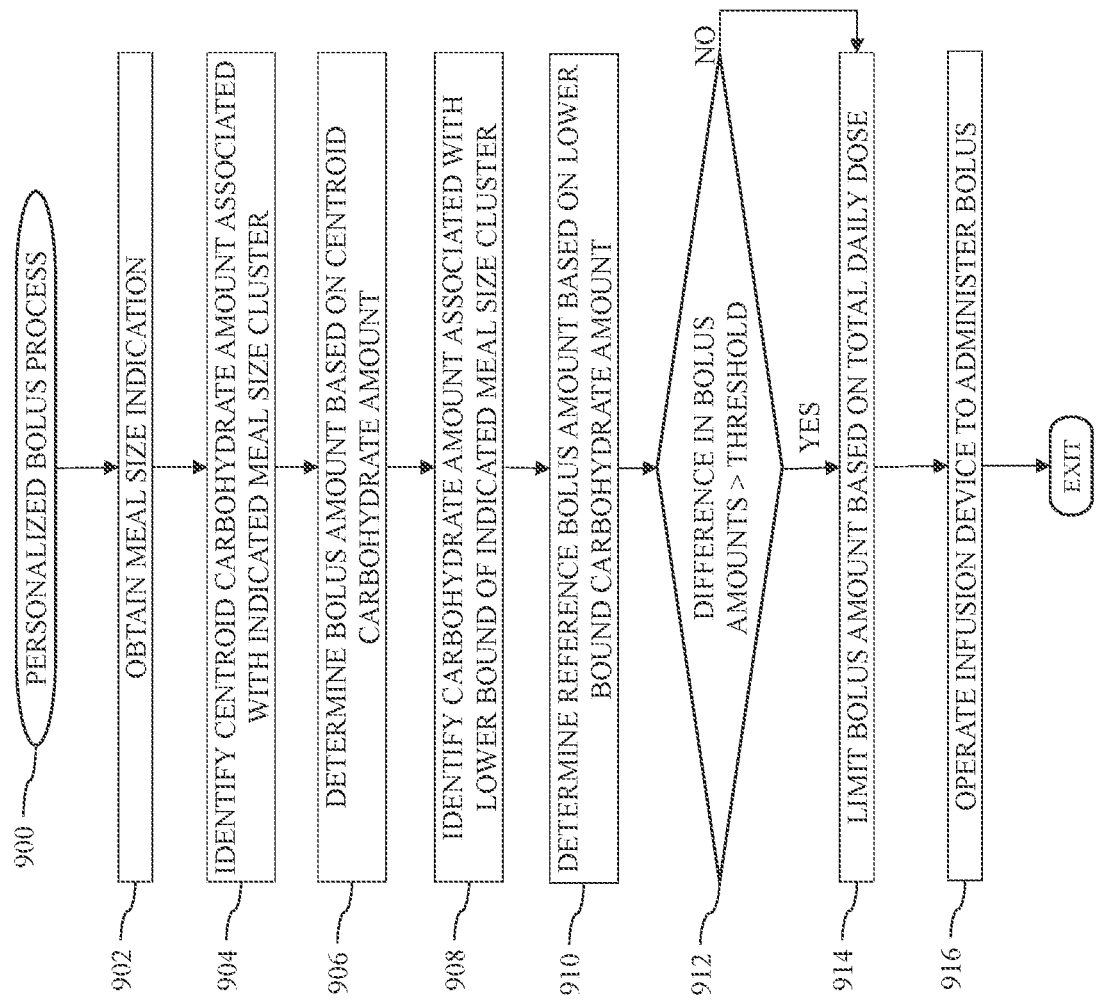
FIG. 9 is a flow diagram of an exemplary personalized bolus process suitable implementation in connection with an infusion device in one or more exemplary embodiments.

FIG. 9 depicts an exemplary embodiment of a personalized bolus process 900 that may be performed to allow a patient to define meal sizes qualitatively in connection with the meal size determination process 500 and clustering process 600 of FIGS. 5-6. The various tasks performed in connection with the personalized bolus process 900 may be performed by hardware, firmware, software executed by processing circuitry, or any combination thereof. For illustrative purposes, the following description refers to elements mentioned above in connection with FIGS. 1-4. In practice, portions of the clustering process 600 may be performed by different elements of an infusion system, such as, for example, an infusion device 102, 202, 402, a client computing device 106, 406, a remote computing device 108, 414, and/or a pump control system 220, 300. It should be appreciated that the personalized bolus process 900 may include any number of additional or alternative tasks, the tasks need not be performed in the illustrated order and/or the tasks may be performed concurrently, and/or the personalized bolus process 900 may be incorporated into a more comprehensive procedure or process having additional functionality not described in detail herein. Moreover, one or more of the tasks shown and described in the context of FIG. 9 could be omitted from a practical embodiment of the personalized bolus process 900 as long as the intended overall functionality remains intact.

In a similar manner as described above, in exemplary embodiments, personalized bolus process 900 is implemented once sufficient historical meal data and corresponding patient measurement data has been obtained and stored in the database 416 such that the meal size determination process 500 and clustering process 600 may be performed with a desired level of accuracy or reliability. In this regard, prior to the personalized bolus process 900 being implemented or enabled, the patient may estimate or input meal sizes when logging meal events while also manually interacting with a bolus wizard or other feature of the infusion device 102, 202, 402 or a client application 408 on the client device 106, 406 to configure and administer boluses for the contemporaneous meal events. Once sufficient historical meal data exists, the meal size determination process 500 may be performed and the personalized bolus process 900 enabled.

The personalized bolus process 900 begins by receiving or otherwise obtaining an indication of a meal size for the meal to be bolused (task 902). In one or more exemplary embodiments, the personalized bolus process 900 is initiated when the patient interacts with a bolus wizard feature of a particular application 308, 310, 408 used to administer meal boluses. For example, the client application 408 at the client device 406 may generate or otherwise provide a bolus wizard GUI display that includes selectable GUI elements corresponding to different qualitative meal sizes, with the patient manipulating the client device 406 to select the meal size to be assigned to the current meal. In this regard, in exemplary embodiments, the GUI display includes a list of the different qualitative meal size cluster groups identified for the patient, with each qualitative meal size having a corresponding selectable GUI element that includes the name or other description of the respective qualitative meal size associated with that GUI element along with one or more quantitative attributes associated with the respective qualitative meal size. For example, for the patient having the prior meal events depicted in FIG. 7, the bolus wizard GUI display may include a button (or similar selectable GUI element) associated with the smallest meal size (e.g., cluster 702) that includes the text "Small" within the button along with indication of the lower and upper carbohydrate bounds associated with the "Small" meal size (e.g., "10 to <30 grams"), along with another button displayed adjacent to the "Small" meal size button that corresponds to the next larger meal size (e.g., cluster 704) includes the text "Medium" within the button along with indication of the lower and upper carbohydrate bounds associated with the "Medium" meal size (e.g., "30 to <45 grams"), and so on. In yet other embodiments, the personalized bolus process 900 is automatically initiated in response to detecting a meal event pattern to calculate a meal bolus dosage based on the predicted meal, where the input meal size corresponds to the predicted meal size based on the patient's historical meal data, as described in United States Patent Application Publication No. 2018/0169334, which is hereby incorporated by reference herein.

In response to a qualitative meal size indication, the personalized bolus process 900 continues by identifying or otherwise determining a centroid carbohydrate amount associated with the identified qualitative meal size cluster group and calculating or otherwise determining a corresponding bolus amount of insulin based on the centroid carbohydrate amount (tasks 904, 906). For example, for the patient having the prior meal events depicted in FIG. 7, in response to selection of the "Small" meal size button from the bolus wizard GUI display, the personalized bolus process 900 may identify the carbohydrate amount associated with the centroid 701 of the selected qualitative meal size cluster group 702 (e.g., 23 grams) for use as the amount of carbohydrates associated with the meal. Thereafter, a corresponding meal bolus dosage of insulin may be determined using the centroid carbohydrate amount and the patient's current carbohydrate ratio, for example, by multiplying the centroid carbohydrate amount by the patient's current carbohydrate ratio (e.g., 23×CR).

As described in United States Patent Application Publication No. 2018/0169334, in some embodiments, the carbohydrate ratio may be estimated for the current time of day and/or the current qualitative meal size based on the patient's historical meal data. For example, based on the relationship between the historical meal data associated with the previous meal events and the corresponding historical patient measurement and insulin delivery data, the personalized bolus process 900 may calculate or otherwise determine a patient-specific carbohydrate ratio associated with the input meal size that accounts for variability of the actual meal size and other factors (e.g., time of day, day of the weak, nutritional components and consumption order for the meal, etc.) that affect the rate of glucose appearance. In this regard, a mathematical model of the patient's postprandial glucose response to meals having the input qualitative meal size may be created using the patient's historical sensor glucose measurement values for postprandial periods following the respective meal events assigned to that qualitative meal size cluster group, historical meal bolus dosages of insulin associated with the respective meal events assigned to that qualitative meal size cluster group, and historical closed-loop or basal insulin deliveries for postprandial and/or preprandial periods surrounding the respective meal events assigned to that qualitative meal size cluster group. An average or nominal glucose rate of appearance for the input meal size may be determined based on the historical sensor glucose measurement values and utilized to determine an estimated postprandial peak in the patient's sensor glucose value following a meal event. The mathematical model may then be optimized to identify an estimated carbohydrate ratio for the input meal size that results in an average estimated postprandial peak sensor glucose value at the estimated postprandial peak time following a meal event equal to a desired target postprandial peak sensor glucose value (e.g., 180 mg/dL). In other embodiments, a heuristic statistical analysis may be performed on the patient's historical meal, delivery, and measurement data to identify a carbohydrate ratio for the input meal size that is likely to achieve a desired postprandial glucose response. It should be noted that in some embodiments, the historical data sets utilized to determine the carbohydrate ratio may be further filtered or limited to be context-specific, for example, to particular periods of the day (e.g., meal events corresponding to a morning period between 6:00 A.M. and 12:00 P.M.), a particular day of the week, a particular geographic location, and/or the like.

Still referring to FIG. 9, in exemplary embodiments, the personalized bolus process 900 continues by identifying or otherwise determining a lower carbohydrate boundary associated with the identified qualitative meal size cluster group and calculating or otherwise determining a corresponding reference bolus amount of insulin based on the lower boundary carbohydrate amount (tasks 908, 910). For example, for the patient having the prior meal events depicted in FIG. 7, in response to selection of the "Small"

meal size button from the bolus wizard GUI display, the personalized bolus process 900 may identify the lower boundary carbohydrate amount for the selected qualitative meal size cluster group 702 (e.g., 10 grams) and determine a corresponding reference bolus dosage of insulin using the lower boundary carbohydrate amount and the patient's current carbohydrate ratio (e.g., 10×CR).

Thereafter, in the illustrated embodiment, the personalized bolus process 900 verifies or otherwise confirms whether or not the difference between the meal bolus dosage based on the centroid carbohydrate amount for the qualitative meal size cluster group and the reference bolus dosage based on the lower boundary carbohydrate amount for the qualitative meal size cluster group is less than a safety threshold (task 912). In this regard, the safety threshold is chosen to account for the variability or distribution of the patient's prior meal events assigned to the selected meal size cluster to mitigate or otherwise reduce the likelihood of delivering excess insulin in the event the current meal is towards the lower end of the qualitative meal size range. For example, in one embodiment, the safety threshold is chosen to be equal to five percent of the patient's total daily dose of insulin. When the difference between the meal bolus dosage based on the centroid carbohydrate amount for the qualitative meal size cluster group and the reference bolus dosage is greater than the safety threshold (e.g., 23×CR−10× CR>0.05×TDD), the personalized bolus process 900 limits or otherwise reduces the meal bolus dosage using the patient's total daily dose (task 914). For example, the personalized bolus process 900 may cap the meal bolus dosage to the sum of the reference bolus dosage and the safety threshold, that is, continuing the above example, the sum of the reference bolus dosage plus five percent of the patient's total daily dose of insulin (e.g., 10×CR+0.05× TDD).

After verifying the meal bolus dosage amount determined based on the qualitative meal size cluster group is safe, the personalized bolus process 900 continues by operating the infusion device to administer the resulting meal bolus dosage amount (task 916). In this regard, the command generation application 310 is then commanded, signaled, or otherwise instructed to operate the motor 232 of the infusion device 202 to deliver the calculated bolus dosage of insulin. In some embodiments, the calculated meal bolus dosage may be automatically administered; however, in other embodiments, a notification of the calculated meal bolus dosage may be generated or otherwise provided on a GUI display for review, modification, and/or confirmation by the patient. Such a GUI display may also include indication of the estimated carbohydrate ratio and centroid carbohydrate amount for review, modification, and/or confirmation. In this regard, some embodiments may allow the patient to override the personalized bolus process 900 and modify one or more of the carbohydrate ratio, the carbohydrate amount, or the bolus dosage amount.

By virtue of the carbohydrate ratio and the centroid carbohydrate amounts being personalized and based on the patient's historical meal, delivery, and measurement data, the meal bolus accounts for variations in the rate of glucose appearance for the patient along with variations in the actual quantitative meal size relative to the input qualitative meal size. This allows the patient to merely input a qualitative meal size rather than having to resort to carbohydrate counting while still providing a meal bolus dosage that maintains safe and effective postprandial glucose management.

Diabetes Data Management System Overview

Figure 10:
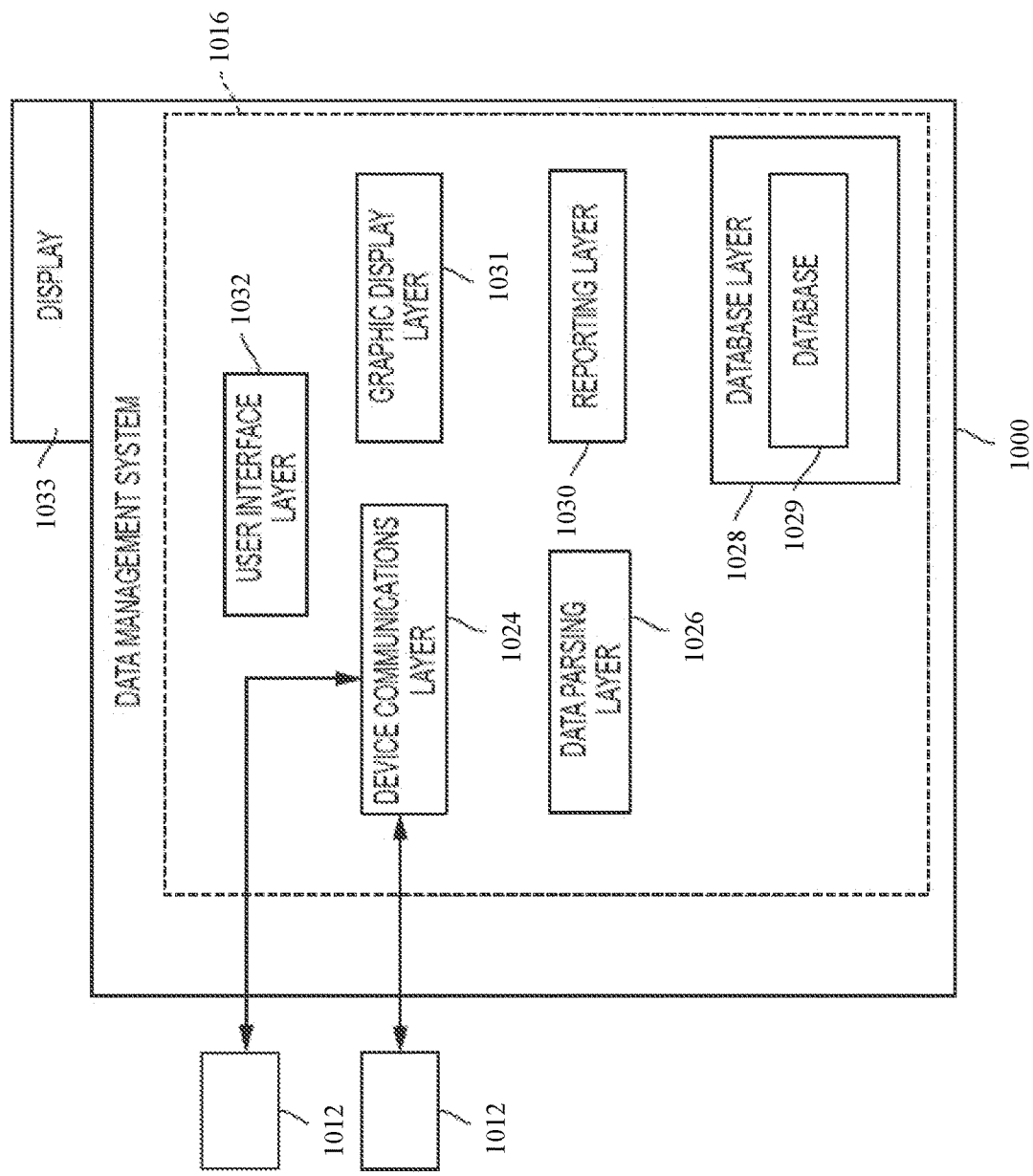
FIG. 10 depicts an embodiment of a computing device of a diabetes data management system suitable for use in connection with any one or more of the systems of FIGS. 1, 2 and 4 and any one or more of the processes of FIGS. 5, 6 and 9 in accordance with one or more embodiments.

FIG. 10 illustrates a computing device 1000 suitable for use as part of a diabetes data management system in conjunction with one or more of the processes described above in the context of FIGS. 5-9. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments are made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 1000. The computing device 1000 may be coupled to a display 1033. In some embodiments, the computing device 1000 may be in a physical device separate from the display (such as in a personal computer, a mini-computer, etc.) In some embodiments, the computing device 1000 may be in a single physical enclosure or device with the display 1033 such as a laptop where the display 1033 is integrated into the computing device. In embodiments of the invention, the computing device 1000 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 1000 may also be a server located on the Internet that is accessible via a browser installed on a laptop computer, desktop computer, a network computer, or a PDA. The computing device 1000 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 10, the data management system 1016 comprises a group of interrelated software modules or layers that specialize in different tasks. The system software includes a device communication layer 1024, a data parsing layer 1026, a database layer 1028, database storage devices 1029, a reporting layer 1030, a graph display layer 1031, and a user interface layer 1032. The diabetes data management system may communicate with a plurality of subject support devices 1012, two of which are illustrated in FIG. 10. Although the different reference numerals refer to a number of layers, (e.g., a device communication layer, a data parsing layer, a database layer), each layer may include a single software module or a plurality of software modules. For example, the device communications layer 1024 may include a number of interacting software modules, libraries, etc. In embodiments of the invention, the data management system 1016 may be installed onto a non-volatile storage area (memory such as flash memory, hard disk, removable hard, DVD-RW, CD-RW) of the computing device 1000. If the data management system 1016 is selected or initiated, the system 1016 may be loaded into a volatile storage (memory such as DRAM, SRAM, RAM, DDRAM) for execution.

The device communication layer 1024 is responsible for interfacing with at least one, and, in further embodiments, to a plurality of different types of subject support devices 1012, such as, for example, blood glucose meters, glucose sensors/monitors, or an infusion pump. In one embodiment, the device communication layer 1024 may be configured to communicate with a single type of subject support device 1012. However, in more comprehensive embodiments, the device communication layer 1024 is configured to communicate with multiple different types of subject support devices 1012, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 1012, the diabetes data management system 1016 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 1024 allows the DDMS 1016 to receive information from and transmit information to or from each subject support device 1012 in the system 1016. Depending upon the embodiment and context of use, the type of information that may be communicated between the system 1016 and device 1012 may include, but is not limited to, data, programs, updated software, education materials, warning messages, notifications, device settings, therapy parameters, or the like. The device communication layer 1024 may include suitable routines for detecting the type of subject support device 1012 in communication with the system 1016 and implementing appropriate communication protocols for that type of device 1012. Alternatively, or in addition, the subject support device 1012 may communicate information in packets or other data arrangements, where the communication includes a preamble or other portion that includes device identification information for identifying the type of the subject support device. Alternatively, or in addition, the subject support device 1012 may include suitable user-operable interfaces for allowing a user to enter information (e.g., by selecting an optional icon or text or other device identifier) that corresponds to the type of subject support device used by that user. Such information may be communicated to the system 1016, through a network connection. In yet further embodiments, the system 1016 may detect the type of subject support device 1012 it is communicating with in the manner described above and then may send a message requiring the user to verify that the system 1016 properly detected the type of subject support device being used by the user. For systems 1016 that are capable of communicating with multiple different types of subject support devices 1012, the device communication layer 1024 may be capable of implementing multiple different communication protocols and selects a protocol that is appropriate for the detected type of subject support device.

The data-parsing layer 1026 is responsible for validating the integrity of device data received and for inputting it correctly into a database 1029. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 1016 may compare received identification information with pre-stored information to evaluate whether the received information is from a valid source.

The database layer 1028 may include a centralized database repository that is responsible for warehousing and archiving stored data in an organized format for later access, and retrieval. The database layer 1028 operates with one or more data storage device(s) 1029 suitable for storing and providing access to data in the manner described herein. Such data storage device(s) 1029 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 1016 or other entities, for analyzing group data or other forms of conglomerate data.

Embodiments of the database layer 1028 and other components of the system 1016 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 1028 may be configured to limit access of each user to types of information pre-authorized for that user. For example, a subject may be allowed access to his or her individual medical information (with individual identifiers) stored by the database layer 1028, but not allowed access to other subject's individual medical information (with individual identifiers). Similarly, a subject's authorized healthcare provider or payor entity may be provided access to some or all of the subject's individual medical information (with individual identifiers) stored by the database layer 1028, but not allowed access to another individual's personal information. Also, an operator or administrator-user (on a separate computer communicating with the computing device 1000) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 1028 in the data storage devices 1029.

In exemplary embodiments, the database 1029 stores uploaded measurement data for a patient (e.g., sensor glucose measurement and characteristic impedance values) along with event log data consisting of event records created during a monitoring period corresponding to the measurement data. In embodiments of the invention, the database layer 1028 may also store preference profiles. In the database layer 1028, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 1029 in the database layer. Preference profiles may include various threshold values, monitoring period values, prioritization criteria, filtering criteria, and/or other user-specific values for parameters to generate a snapshot GUI display on the display 1033 or a support device 1012 in a personalized or patient-specific manner.

The DDMS 1016 may measure, analyze, and track either blood glucose (BG) or sensor glucose (SG) measurements (or readings) for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 1030 may include a report wizard program that pulls data from selected locations in the database 1029 and generates report information from the desired parameters of interest. The reporting layer 1030 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 1030 also facilitates generation of a snapshot report including a snapshot GUI display.

In embodiments of the invention, the database layer 1028 may calculate values for various medical information that is to be displayed on the reports generated by the report or reporting layer 1030. For example, the database layer 1028, may calculate average blood glucose or sensor glucose readings for specified timeframes. In embodiments of the invention, the reporting layer 1030 may calculate values for medical or physical information that is to be displayed on the reports. For example, a user may select parameters which are then utilized by the reporting layer 1030 to generate medical information values corresponding to the selected parameters. In other embodiments of the invention, the user may select a parameter profile that previously existed in the database layer 1028.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 1016 into further reporting tools familiar to the user. The reporting layer 1030 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 1030 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 1016 may allow a user generating a report to designate the report as non-printable and/or non-transferable, whereby the system 1016 will provide the report in a form that inhibits printing and/or electronic transfer.

The reporting layer 1030 may transfer selected reports to the graph display layer 1031. The graph display layer 1031 receives information regarding the selected reports and converts the data into a format that can be displayed or shown on a display 1033.

In embodiments of the invention, the reporting layer 1030 may store a number of the user's parameters. Illustratively, the reporting layer 1030 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 1032 supports interactions with the end user, for example, for user login and data access, software navigation, data input, user selection of desired report types and the display of selected information. Users may also input parameters to be utilized in the selected reports via the user interface layer 1032. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 1032 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 1016, depending upon the embodiment of use.

In another example embodiment, where the DDMS 1016 is located on one computing device 1000, the user interface layer 1032 provides a number of menus to the user to navigate through the DDMS. These menus may be created utilizing any menu format, including but not limited to HTML, XML, or Active Server pages. A user may access the DDMS 1016 to perform one or more of a variety of tasks, such as accessing general information made available on a website to all subjects or groups of subjects. The user interface layer 1032 of the DDMS 1016 may allow a user to access specific information or to generate reports regarding that subject's medical condition or that subject's medical device(s) 1012, to transfer data or other information from that subject's support device(s) 1012 to the system 1016, to transfer data, programs, program updates or other information from the system 1016 to the subject's support device(s) 1012, to manually enter information into the system 1016, to engage in a remote consultation exchange with a healthcare provider, or to modify the custom settings in a subject's supported device and/or in a subject's DDMS/MDMS data file.

The system 1016 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 1016 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 1016, based on the type of user and/or the identity of the user.

Upon entering successful verification of the user's identification information and password, the user may be provided access to secure, personalized information stored on the DDMS 1016. For example, the user may be provided access to a secure, personalized location in the DDMS 1016 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 1012 to the system 1016, manually enter additional data into the system 1016, modify the subject's custom settings, and/or view and print reports. Reports may include data specific to the subject's condition, including but not limited to, data obtained from the subject's subject support device(s) 1012, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 1029) employed by the database layer 1028.

The user may select an option to transfer (send) device data to the medical data management system 1016. If the system 1016 receives a user's request to transfer device data to the system, the system 1016 may provide the user with step-by-step instructions on how to transfer data from the subject's supported device(s) 1012. For example, the DDMS 1016 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 1012 used by the subject. The system 1016 employs that information to select the stored instruction set(s) associated with the particular subject's support device(s) 1012 for display to the user.

Other activities or resources available to the user on the system 1016 may include an option for manually entering information to the DDMS/MDMS 1016. For example, from the user's personalized menu or location, the user may select an option to manually enter additional information into the system 1016.

Further optional activities or resources may be available to the user on the DDMS 1016. For example, from the user's personalized menu, the user may select an option to receive data, software, software updates, treatment recommendations or other information from the system 1016 on the subject's support device(s) 1012. If the system 1016 receives a request from a user to receive data, software, software updates, treatment recommendations or other information, the system 1016 may provide the user with a list or other arrangement of multiple selectable icons or other indicia representing available data, software, software updates or other information available to the user.

Yet further optional activities or resources may be available to the user on the medical data management system 1016 including, for example, an option for the user to customize or otherwise further personalize the user's personalized location or menu. In particular, from the user's personalized location, the user may select an option to customize parameters for the user. In addition, the user may create profiles of customizable parameters. When the system 1016 receives such a request from a user, the system 1016 may provide the user with a list or other arrangement of multiple selectable icons or other indicia representing parameters that may be modified to accommodate the user's preferences. When a user selects one or more of the icons or other indicia, the system 1016 may receive the user's request and makes the requested modification.

In one or more exemplary embodiments, for an individual patient in the DDMS, the computing device 1000 of the DDMS is configured to analyze that patient's historical measurement data, historical delivery data, historical event log data, and any other historical or contextual data associated with the patient maintained in the database layer 1028 to support one or more of the processes of FIGS. 5-9. In this regard, machine learning, artificial intelligence, or similar mathematical modeling of the patient's physiological behavior or response may be performed at the computing device 1000 to facilitate patient-specific correlations or predictions. Current measurement data, delivery data, and event log data associated with the patient along with current contextual data may be analyzed using the resultant models, either at the computing device 1000 of the DDMS or another device 1012 to determine probable events, behaviors, or responses by the patient in real-time and perform corresponding delivery adjustments in a manner that is influenced by a correlative subset of the patient's historical data. As a result, patient outcomes may be improved while reducing the burden on the patient to make such patient-specific adjustments.

For the sake of brevity, conventional techniques related to glucose sensing and/or monitoring, sensor calibration and/or compensation, bolusing, machine learning and/or artificial intelligence, clustering, pharmodynamic modeling, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating an infusion device capable of delivering insulin to a patient, the method comprising:
   receiving, by a control system associated with the infusion device, an input qualitative meal size via a user interface;
   categorizing historical meal events for the patient into a plurality of different groups;
   identifying, by the control system, a patient-specific carbohydrate amount representative of the categorized subset of historical meal events for the patient associated with the input qualitative meal size;
   determining, by the control system, a bolus dosage of the insulin for the input qualitative meal size based at least in part on the patient-specific carbohydrate amount; and
   operating, by the control system, the infusion device to deliver the bolus dosage of the insulin to the patient.

2. The method of claim 1, wherein identifying the patient-specific carbohydrate amount comprises determining the patient-specific carbohydrate amount associated with a centroid of the clustered subset of historical meal events.

3. The method of claim 2, wherein each group of the plurality of different groups is associated with a respective qualitative meal size of a plurality of qualitative meal sizes and comprises a unique respective subset of the historical meal events assigned to the respective qualitative meal size.

4. The method of claim 1, wherein each group of the plurality of different groups is associated with a respective qualitative meal size of a plurality of qualitative meal sizes and comprises a unique respective subset of the historical meal events assigned to the respective qualitative meal size.

5. The method of claim 4, wherein receiving the input qualitative meal size comprises identifying selection of the input qualitative meal size from among the plurality of qualitative meal sizes.

6. The method of claim 5, further comprising displaying a list of the plurality of qualitative meal sizes, wherein for each respective qualitative meal size, the list includes one or more bounds for carbohydrate amounts of the respective subset of the historical meal events assigned to the respective qualitative meal size.

7. The method of claim 5, further comprising displaying a list of the plurality of qualitative meal sizes, wherein for each respective qualitative meal size, the list includes a centroid carbohydrate amount for the respective subset of the historical meal events assigned to the respective qualitative meal size.

8. The method of claim 4, further comprising:
   identifying, for each historical meal event of the historical meal events, a respective carbohydrate amount associated with the respective historical meal event based on historical meal data associated with the patient; and
   identifying, for each historical meal event of the historical meal events, a respective value for a variable associated with the respective historical meal event based on historical measurement data associated with the patient, wherein clustering the historical meal events comprises clustering the historical meal events into the plurality of different groups based on relationships between the respective carbohydrate amounts and the respective values for the variable associated with the historical meal events.

9. The method of claim 8, wherein the patient-specific carbohydrate amount comprises a centroid carbohydrate amount for the clustered subset of historical meal events associated with the input qualitative meal size.

10. The method of claim 1, wherein determining the bolus dosage comprises:
    determining a dosage of insulin based at least in part on the patient-specific carbohydrate amount and a carbohydrate ratio;
    determining a reference dosage of insulin for the input qualitative meal size based at least in part on a minimum carbohydrate amount from among the clustered subset of historical meal events and the carbohydrate ratio; and
    limiting the bolus dosage when a difference between the determined dosage and the reference dosage is greater than a threshold.

11. The method of claim 10, further comprising determining the threshold based at least in part on a total daily dose of insulin for the patient, wherein limiting the bolus dosage comprises limiting the bolus dosage to a sum of the threshold and the reference dosage of insulin for the input qualitative meal size.

12. The method of claim 10, further comprising:
    obtaining historical meal data corresponding to the clustered subset of historical meal events associated with the input qualitative meal size; and
    estimating the carbohydrate ratio based at least in part on the historical meal data.

13. A method of operating an infusion device capable of delivering fluid to a patient, the method comprising:
    categorizing historical events associated with a patient into a plurality of groups, wherein each group of the plurality of groups is associated with a respective qualitative event attribute of a plurality of qualitative event attributes;
    obtaining, by a control system associated with the infusion device, a qualitative event attribute from among the plurality of qualitative event attributes;
    obtaining, by the control system, a quantitative event attribute associated with the qualitative event attribute, wherein the quantitative event attribute is representative of the group of historical events for the patient associated with the qualitative event attribute; and
    determining, by the control system, a dosage of the fluid based at least in part on the quantitative event attribute.

14. The method of claim 13, further comprising displaying a list of the plurality of qualitative event attributes, wherein the list comprises a respective quantitative event attribute associated with each respective qualitative event attribute of the plurality of qualitative event attributes.

15. The method of claim 14, further comprising determining, for each respective qualitative event attribute of the plurality of qualitative event attributes, the respective quantitative event attribute associated with the respective qualitative event attribute based on a centroid of a respective group of the historical events categorized into the respective group of the plurality of groups, wherein:
    the qualitative event attribute comprises a qualitative meal size; the historical events comprise historical meal events; and
    the quantitative event attribute comprises a carbohydrate amount associated with the centroid of the respective group of the historical meal events categorized into the respective group associated with the qualitative meal size.

16. The method of claim 13, wherein:
    the plurality of qualitative event attributes comprise a plurality of qualitative meal sizes;
    the qualitative event attribute comprises an input qualitative meal size of the plurality of qualitative meal sizes;
    the quantitative event attribute comprises a carbohydrate amount associated with the input qualitative meal size;
    the historical events comprise historical meal events;
    the fluid comprises insulin; and
    the method further comprises:
        identifying, for each historical meal event of the historical meal events, a respective carbohydrate amount associated with the respective historical meal event based on historical meal data; and
        identifying, for each historical meal event of the historical meal events, a respective value for a variable associated with the respective historical meal event based on historical measurement data associated with the patient, wherein categorizing the historical events comprises clustering the historical meal events into the plurality of groups based on relationships between the respective carbohydrate amounts and the respective values for the variable associated with the historical meal events.

17. The method of claim 16, further comprising determining the carbohydrate amount associated with the input qualitative meal size based on a centroid of the respective group of historical meal events clustered into the respective group associated with the input qualitative meal size.

18. The method of claim 13, wherein determining the dosage of the fluid comprises:
    determining a reference dosage of the fluid based at least in part on a minimum quantitative event attribute associated with a lower bound of the group of historical events; and
    limiting the dosage when a difference between the dosage and the reference dosage is greater than a threshold.

19. An infusion system comprising:
    an actuation arrangement operable to deliver insulin to a patient;
    a user interface to receive an input qualitative meal size;
    a data storage element to maintain historical meal data associated with historical meal events for the patient, the historical meal events for the patient categorized into a plurality of different groups, wherein each group of the plurality of different groups is associated with a respective qualitative meal size of a plurality of qualitative meal sizes and comprises a unique respective subset of the historical meal events assigned to the respective qualitative meal size; and
    a control system coupled to the actuation arrangement, the user interface, and the data storage element and configured to:
        identify a patient-specific carbohydrate amount representative of a categorized subset of the historical meal events corresponding to a particular group among the plurality of different groups that is associated with the input qualitative meal size,
        determine a meal bolus dosage of the insulin for the input qualitative meal size based at least in part on the patient-specific carbohydrate amount, and operate the actuation arrangement to deliver the meal bolus dosage of the insulin to the patient.

\* \* \* \* \*